United States Patent
Stone

(10) Patent No.: US 8,932,575 B2
(45) Date of Patent: Jan. 13, 2015

(54) COMPOSITIONS AND METHODS FOR INDUCING MIGRATION BY DENDRITIC CELLS AND AN IMMUNE RESPONSE

(75) Inventor: Geoffrey William Stone, Coral Gables, FL (US)

(73) Assignee: University Of Miami, Miami, FL (US)

(*) Notice: Subject to any disclaimer, the term of this patent is extended or adjusted under 35 U.S.C. 154(b) by 47 days.

(21) Appl. No.: 13/825,078

(22) PCT Filed: Sep. 19, 2011

(86) PCT No.: PCT/US2011/052138
§ 371 (c)(1),
(2), (4) Date: May 28, 2013

(87) PCT Pub. No.: WO2012/040101
PCT Pub. Date: Mar. 29, 2012

(65) Prior Publication Data
US 2013/0243724 A1 Sep. 19, 2013

Related U.S. Application Data

(60) Provisional application No. 61/384,779, filed on Sep. 21, 2010.

(51) Int. Cl.
*A01N 63/00* (2006.01)
*A61K 48/00* (2006.01)
*C12N 5/0784* (2010.01)
*A61K 38/16* (2006.01)
*A61K 39/00* (2006.01)
*A61K 39/39* (2006.01)
*A61K 45/06* (2006.01)
*A61K 38/19* (2006.01)
*A61K 38/20* (2006.01)
*A61K 35/14* (2006.01)
*A61K 39/245* (2006.01)
*C12N 15/85* (2006.01)

(52) U.S. Cl.
CPC ............ *C12N 5/0639* (2013.01); *A61K 38/162* (2013.01); *A61K 39/0011* (2013.01); *A61K 39/39* (2013.01); *A61K 45/06* (2013.01); *A61K 38/191* (2013.01); *A61K 38/2006* (2013.01); *A61K 38/204* (2013.01); *A61K 35/15* (2013.01); *A61K 39/245* (2013.01); *C12N 15/85* (2013.01); *A61K 2039/5154* (2013.01); *A61K 2039/5156* (2013.01); *A61K 2039/55511* (2013.01); *C12N 2710/10043* (2013.01); *C12N 2710/10071* (2013.01)
USPC ........................................ 424/93.2; 424/93.1

(58) Field of Classification Search
CPC ............................... A61K 35/12; C12N 15/86
USPC ............................................... 424/93.1, 93.2
See application file for complete search history.

(56) References Cited

U.S. PATENT DOCUMENTS

| 7,655,235 | B2 | 2/2010 | Ertl |
| 2004/0197305 | A1 | 10/2004 | Garzino-Demo et al. |
| 2008/0145375 | A1* | 6/2008 | Bembridge et al. ....... 424/184.1 |
| 2009/0053252 | A1 | 2/2009 | Tschopp et al. |
| 2009/0053299 | A1 | 2/2009 | Chang et al. |
| 2009/0069256 | A1 | 3/2009 | Smith et al. |
| 2009/0081157 | A1 | 3/2009 | Kornbluth et al. |
| 2009/0208531 | A1 | 8/2009 | Nabel et al. |
| 2009/0238841 | A1 | 9/2009 | Donnelly et al. |
| 2009/0305324 | A1* | 12/2009 | Kuzushima et al. ............ 435/29 |
| 2010/0166787 | A1 | 7/2010 | Weiner et al. |
| 2010/0199364 | A1 | 8/2010 | Hill et al. |

OTHER PUBLICATIONS

Gottschalk et al. cited on IDS.*
Wu et al. (2005, JBC, vol. 280, pp. 33620-33626).*
Kondo et al. (2007, J. Virology, vol. 81(4), pp. 1554-1562).*
Kandil et al. (2005, Clin. Exp. Imm. vol. 140, p. 54-64).*
Barratt-Boyes et al. (2000, J. Immunology, vol. 164, pp. 2487-2495).*
Bolesta et al., "Increased level and longevity of protective immune responses induced by DNA vaccine expressing the HIV-1 Env glycoprotein when combined with IL-21 and IL-15 gene delivery," J Immunology (2006) 177(1):177-191.
Caputo et al., "HIV-1 Tat-based vaccines: An overview and perspectives in the field of HIV/AIDS vaccine development," Int Rev Immunol (2009) 28(5): 285-334.
Cerutti et al., "Role of BAFF and APRIL in antibody production and diversification," Contemporary Immunology. BLyS Ligands and Receptors ePub (2009) 65-92.
Gherardi et al., "IL-21 delivery from recombinant vaccinia virus attenuates the vector and enhances the cellular immune response against HIV-1 Env in a dose-dependent manner," J Immunol (1999) 162(11): 6724-6733.
Gottschalk et al., "Generating CTLs against the subdominant Epstein-Barr virus LMP1 antigen for the adoptive immunotherapy of EBV-associated malignancies," Blood (2003) 101(5): 1905-1912.
Hanlon et al., "Feline leukemia virus DNA vaccine efficacy is enhanced by coadministration with interleukin-12 (IL-12) and IL-18 expression vectors," J Virol (2001) 75(18): 8424-8433.

(Continued)

*Primary Examiner* — Anoop Singh
*Assistant Examiner* — David A Montanari
(74) *Attorney, Agent, or Firm* — Novak Druce Connolly Bove + Quigg LLP

(57) ABSTRACT

Compositions and methods of activating dendritic cells with LMP1 and LMP1-activated dendritic cell based compositions and methods are effective for dendritic cell therapy and provide an adjuvant function for vaccine administration. LMP1 or LMP1-CD40 chimeric protein may be used to activate and mature dendritic cells. LMP1 and LMP1-activated dendritic cells act as an adjuvant to enhance the cellular immune response. Also disclosed herein are kits for activating dendritic cells and for preparing a vaccine formulation. Administration of the dendritic cells transfected with LMP1 can induce an immune response against cancer or infection. The mature dendritic cells may comprise an antigen and at least one cytokine in addition to LMP1. Use of LMP1 or LMP1-CD40 provides a way to activate and mature dendritic cells that retain functional and migratory abilities without the side effects that result from maturing the dendritic cells using $PGE_2$.

8 Claims, 23 Drawing Sheets

(56) References Cited

OTHER PUBLICATIONS

Hatzivassiliou et al., "A fusion of the EBV latent membrane protein-1 (LMP1) transmembrane domains to the CD40 cytoplasmic domain is similar to LMP1 in constitutive activation of epidermal growth factor receptor expression, nuclear factor-kappa B, and stress-activated protein kinase," J Immunol (1998) 160(3): 1116-1122.

He et al., "HIV-1 envelope triggers polyconal Ig class switch recombination through a CD40-independent mechanism involving BAFF and C-type lectin receptors," J Immunol (2006) 176(7): 3931-3941.

Mailliard et al., "Alpha-type-1 polarized dendritic cells: A novel immunization tool with optimized CTL-inducing activity," Cancer Res (2004) 64(17): 5934-5937.

Morrow et al., "Comparative ability of IL12 and IL28B to regulate Treg populations and enhance adaptive cellular immunity," Blood (2009) 113(23):5868-5877.

Rodrigues et al., "IL-21 and IL-15 cytokine DNA augments HSV specific effector and memory CD8+ T cell response," Mol Immunol (2009) 46(7):1494-1504.

Stone et al., "Macaque multimeric soluble CD40 ligand and GITR ligand constructs are immunostimulatory molecules in vitro," Clin Vaccine Immunol (2006) 13(11):1223-1230.

Stone et al., "Multimeric soluble CD40 ligand and GITR ligand as adjuvants for human immunodeficiency virus DNA vaccines," J Virol (2006) 80(4): p. 1762-1772.

* cited by examiner

COMPOSITIONS AND METHODS FOR INDUCING MIGRATION BY DENDRITIC CELLS AND AN IMMUNE RESPONSE

CROSS REFERENCE TO RELATED APPLICATIONS

This is a 371 National Stage Application of International Application No. PCT/US11/52138, filed Sep. 19, 2011, which claims priority to U.S. Provisional Application No. 61/384,779, filed Sep. 21, 2010, the entireties of which are incorporated herein by reference.

STATEMENT REGARDING FEDERALLY SPONSORED RESEARCH OR DEVELOPMENT

This invention was made with government support under AI 078834 awarded by the National Institutes of Health. The government has certain rights in the invention.

FIELD OF THE INVENTION

The invention relates generally to the field of immunology. More particularly, the invention relates to compositions, methods, and kits for dendritic cell therapy.

BACKGROUND

Immune activation induces activation and maturation of dendritic cells. Dendritic cells are a part of the immune system that act as antigen-presenting cells. Dendritic cells process antigen material and present it on their cell surface. The antigen material may be from viruses and bacteria.

Immature dendritic cells become activated after detecting an antigen. The antigen protein is degraded by the dendritic cell and the fragments are presented on the surface of the dendritic cell. After the dendritic call is activated, it migrates to the lymph nodes and displays the antigen to other immune system cells.

Cytokine mixes currently used to activate and mature dendritic cells are sub-optimal. These mixes typically include a combination of one or more of: interleukin-1β (IL-1β), tumor necrosis factor-α (TNFα), interleukin-6 (IL-6), interferon-γ (IFN-γ), type I interferon, lipopolysaccharide (LPS), and prostaglandin $E_2$ ($PGE_2$). In some cases, the cytokine mix matures the dendritic cell, but does not induce the migration of the dendritic cell to the lymphoid organs where T cells are activated. In other cases, the cytokine mix can induce migration (typically by including $PGE_2$), but the mix prevents important actions by the dendritic cell, such as responsiveness to T cell help, or the costimulatory ligand CD40L, and expression of the cytokine IL-12p70, both of which are required for optimal T cell activation and development of immune memory. $PGE_2$ is also known to induce a Th2 immune response, again limiting the effectiveness of the dendritic cells.

Traditional maturation of monocyte derived dendritic cells (MDDC) requires the addition of $PGE_2$. Although $PGE_2$ provides a mature dendritic cell that is able to home to the draining lymph node, there are many problems with this approach. These include making dendritic cells unable to respond to CD40 stimulation and impairing the ability of the dendritic cell to produce IL-12, a key cytokine for Th1 immune activation in the lymph node. (Gilboa, E., DC-based cancer vaccines. J Clin Invest, 117(5): 1195-203 (2007)). Potential methods to mature MDDC without $PGE_2$ include co-transfection of molecular adjuvants such as tumor necrosis family superfamily ligands (TNFSF ligands). (Kornbluth, R. S. and Stone, G. W., Immunostimulatory combinations: designing the next generation of vaccine adjuvants. J Leukoc Biol, 80(5): 1084-102 (2006); Stone, G. W., et al., Multimeric soluble CD40 ligand and GITR ligand as adjuvants for human immunodeficiency virus DNA vaccines. J Virol, 80(4): 1762-72 (2006)).

There is thus a significant need for a method to activate dendritic cells while retaining the ability of the dendritic cells to migrate and the migrated dendritic cells to induce T cell memory by secreting IL-12.

SUMMARY

Disclosed herein are compositions, kits, and methods of activating dendritic cells with LMP1 and for preparing a vaccine formulation. Also disclosed herein are LMP1-activated dendritic cell based compositions and methods that are effective for dendritic cell therapy and provide an adjuvant function for vaccine administration. Dendritic cells are activated and matured by exposure to LMP1. Alternatively, a LMP1-CD40 chimeric protein may be used to activate and mature the dendritic cells. LMP1 and LMP1-activated dendritic cells act as an adjuvant to enhance the cellular immune response.

Genetic material such as LMP1 RNA or LMP1 DNA may be transfected into dendritic cells. Alternatively, a viral vector may be used to introduce LMP1 into the dendritic cell. A cytokine protein, e.g., IL-1β, TNFα, and IL-6, may also be incubated with the dendritic cell. Using RNA provides the advantage that the RNA cannot integrate into the genome or be maintained in the cell.

The mature dendritic cells may comprise an antigen and at least one cytokine in addition to LMP1. Activated, mature dendritic cells are capable of migrating towards lymph nodes and displaying antigens to other immune system cells. Administration of the dendritic cells transfected with LMP1 to a subject can induce an immune response against cancer or infection. The immune response comprises secretion of IL-12 by the dendritic cells and activation of Th1 cells.

Examples of cancers that may be treated by administration of dendritic cells transfected with LMP1 include, but are not limited to, melanoma, glioma, prostate cancer, and breast cancer. Examples of infections that may be treated by administration of dendritic cells transfected with LMP1 include, but are not limited to, HIV infection and hepatitis C infection.

Use of LMP1 or LMP1-CD40 provides a way to activate and mature dendritic cells that retain functional and migratory abilities without the side effects that result from maturing the dendritic cells using $PGE_2$.

Unless otherwise defined, all technical terms used herein have the same meaning as commonly understood by one of ordinary skill in the art to which this invention belongs.

As used herein, a "nucleic acid" or a "nucleic acid molecule" means a chain of two or more nucleotides such as RNA (ribonucleic acid) and DNA (deoxyribonucleic acid), and chemically-modified nucleotides. The nucleic acid molecule may be purified. A "purified" nucleic acid molecule is one that is substantially separated from other nucleic acid sequences in a cell or organism in which the nucleic acid naturally occurs (e.g., 30, 40, 50, 60, 70, 80, 90, 95, 96, 97, 98, 99, 100% free of contaminants). The terms include, e.g., a recombinant nucleic acid molecule incorporated into a vector, a plasmid, a virus, or a genome of a prokaryote or eukaryote. Examples of purified nucleic acid molecules include cDNAs, fragments of genomic nucleic acid molecules, nucleic acid molecules produced by polymerase chain reaction (PCR), nucleic acid molecules formed by restriction enzyme treatment of genomic nucleic acid molecules, recombinant nucleic acid molecules, and chemically synthesized nucleic acid molecules.

By the term "LMP1 gene," is meant a native Epstein Barr virus LMP1-encoding nucleic acid sequence, e.g., the native Epstein Barr virus LMP1 gene; a nucleic acid having sequences from which a LMP1 cDNA can be transcribed; and/or allelic variants and homologs of the foregoing. The terms encompass double-stranded DNA, single-stranded DNA, and RNA.

By the term "LMP1 protein," is meant an expression product of a LMP1 gene or a protein that shares at least 65% (but preferably 75, 80, 85, 90, 95, 96, 97, 98, or 99%) amino acid sequence identity with the foregoing and displays a functional activity of a native LMP1 protein. A "functional activity" of a protein is any activity associated with the physiological function of the protein.

As used herein, "protein" and "polypeptide" are used synonymously to mean any peptide-linked chain of amino acids, regardless of length or post-translational modification, e.g., glycosylation or phosphorylation. A "fusion protein" is a protein made by translation of an artificial combination of two otherwise separated segments of sequence, e.g., by chemical synthesis or by the manipulation of isolated segments of nucleic acids by genetic engineering techniques.

When referring to a peptide, oligopeptide or protein, the terms "amino acid residue", "amino acid" and "residue" are used interchangably and, as used herein, mean an amino acid or amino acid mimetic joined covalently to at least one other amino acid or amino acid mimetic through an amide bond or amide bond mimetic.

When referring to a nucleic acid molecule, polypeptide, or infectious pathogen, the term "native" refers to a naturally-occurring (e.g., a wild-type (WT)) nucleic acid, polypeptide, or infectious pathogen.

As used herein, the term "antigen" or "immunogen" means a molecule that is specifically recognized and bound by an antibody.

The term "antibody" is meant to include polyclonal antibodies, monoclonal antibodies (mAbs), chimeric antibodies, humanized antibodies, anti-idiotypic (anti-Id) antibodies to antibodies that can be labeled in soluble or bound form, as well as fragments, regions or derivatives thereof, provided by any known technique, such as, but not limited to, enzymatic cleavage, peptide synthesis or recombinant techniques.

As used herein the term "adjuvant" means any material which modulates to enhance the humoral and/or cellular immune response.

As used herein, the terms "displayed", "presented", or "surface exposed" are considered to be synonyms, and refer to antigens or other molecules that are present (e.g., accessible to immune site recognition) at the external surface of a structure such as a cell.

As used herein, "vaccine" includes all prophylactic and therapeutic vaccines.

As used herein, the term "biologic" refers to a wide range of medicinal products such as vaccines, blood and blood components, allergenics, somatic cells, genes expressing a product in gene therapy, tissues, and recombinant therapeutic proteins created by recombinant DNA technology, antibodies, synthetic drugs, and long peptides (polypeptides), synthetic compounds, and (glycol)proteins.

By the phrase "immune response" is meant induction of antibody and/or immune cell-mediated responses specific against an antigen or antigens or allergen(s) or drug or biologic. The induction of an immune response depends on many factors, including the immunogenic constitution of the challenged organism, the chemical composition and configuration of the antigen or allergen or drug or biologic, and the manner and period of administration of the antigen or allergen or drug or biologic. An immune response has many facets, some of which are exhibited by the cells of the immune system (e.g., B-lymphocytes, T-lymphocytes, macrophages, and plasma cells). Immune system cells may participate in the immune response through interaction with an antigen or allergen or other cells of the immune system, the release of cytokines and reactivity to those cytokines. Immune responses are generally divided into two main categories—humoral and cell-mediated. The humoral component of the immune response includes production of antibodies specific for an antigen or allergen or drug or biologic. The cell-mediated component includes the generation of delayed-type hypersensitivity and cytotoxic effector cells against the antigen or allergen.

As used herein, the term "treatment" is defined as the application or administration of a therapeutic agent to a patient, or application or administration of the therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease, or the predisposition toward disease.

The terms "patient" "subject" and "individual" are used interchangeably herein, and mean a mammalian subject who is to be treated, who has been treated, or who is being considered for treatment, with human patients being preferred. In some cases, the methods, kits, and compositions described herein find use in experimental animals, in veterinary applications, and in the development of animal models for disease, including, but not limited to, rodents including mice, rats, and hamsters, as well as non-human primates.

Although compositions, kits, and methods similar or equivalent to those described herein can be used in the practice or testing of the present invention, suitable compositions, kits, and methods are described below. All publications, patent applications, and patents mentioned herein are incorporated by reference in their entirety. In the case of conflict, the present specification, including definitions, will control. The particular embodiments discussed below are illustrative only and not intended to be limiting.

BRIEF DESCRIPTION OF THE DRAWINGS

FIG. 8 shows measurement of in vivo migration of CFSE-labeled DC transfected with Gag mRNA or LMP1 RNA in mice injected intradermally (i.d.) with CFSE-labeled DC. LMP1 mRNA transfected DC (FIGS. 8C and 8D) were able to migrate and were detected as a distinct CFSE+ population. Control Gag treated DC did not migrate.

(FIG. 12A). The migratory ability of DCs was tested using an 8 μm pore Transwell®. (FIG. 12B). 150,000 cells were allowed 90 minutes to migrate in response to CCL19 or CCL21.

(FIG. 13A). The migratory ability of DCs was tested using an 8 μm pore Transwell®. (FIG. 13B). 150,000 cells were allowed 90 minutes to migrate in response to CCL19.

(FIG. 14A). DC's migratory ability were tested using an 8 μm pore Transwell®. (FIG. 14B). 150,000 cells were allowed 90 minutes to migrate in response to CCL19, CCL21, or CXCL12.

(FIG. 15A). Migratory ability was determined using the previously mention Transwell® migration assay in response to CCL19. (FIG. 15B).

DETAILED DESCRIPTION

Disclosed herein are methods of transfecting RNA or other genetic material encoding LMP1 into ex vivo derived dendritic cells (DCs). These dendritic cells have been shown to migrate efficiently toward lymph node chemokines.

The Epstein Barr Virus gene LMP1 encodes a membrane-associated protein that mimics the B-cell and dendritic cell activating protein CD40, or the pattern recognition Toll Like Receptor (TLR) proteins involved in innate immunity. Unlike CD40 or TLR, LMP1 is constitutively active, leading to the constant activation of infected B cells. Therefore, LMP1 is a constitutively active analog of CD40.

Dendritic cells transfected with LMP1 can be used as an effective reagent for dendritic cell therapy, where it will be necessary for the cells to migrate from the site of injection to the local draining lymph node. Transfection is the process of introducing nucleic acids into cells. LMP1 can costimulate the activation of the transfected DC while allowing the transfected DC to induce T cell memory with secretion of IL-12 cytokines.

Figure 1:
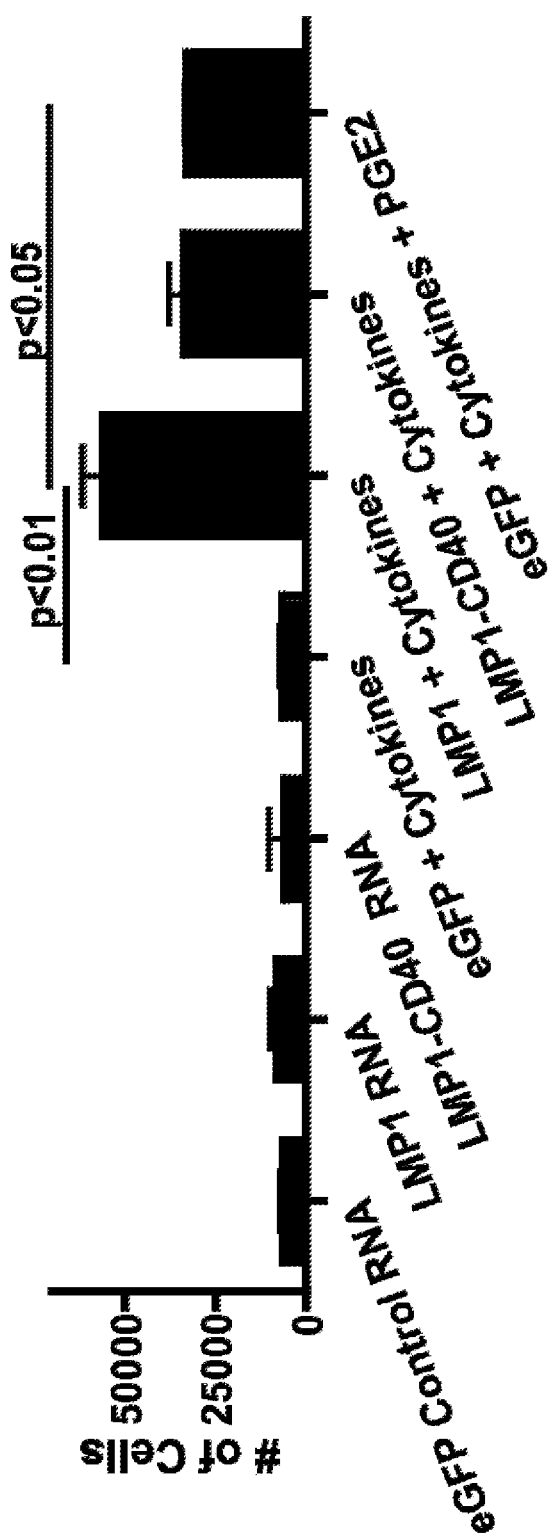
FIG. 1 is a graph showing migration of dendritic cells electroporated with LMP1, LMP1-CD40, or control (eGFP) RNA in the presence or absence of cytokines or $PGE_2$. Migration towards a mixture of lymph node chemokines CCL19 and CCL21 was measured.
Figure 2:
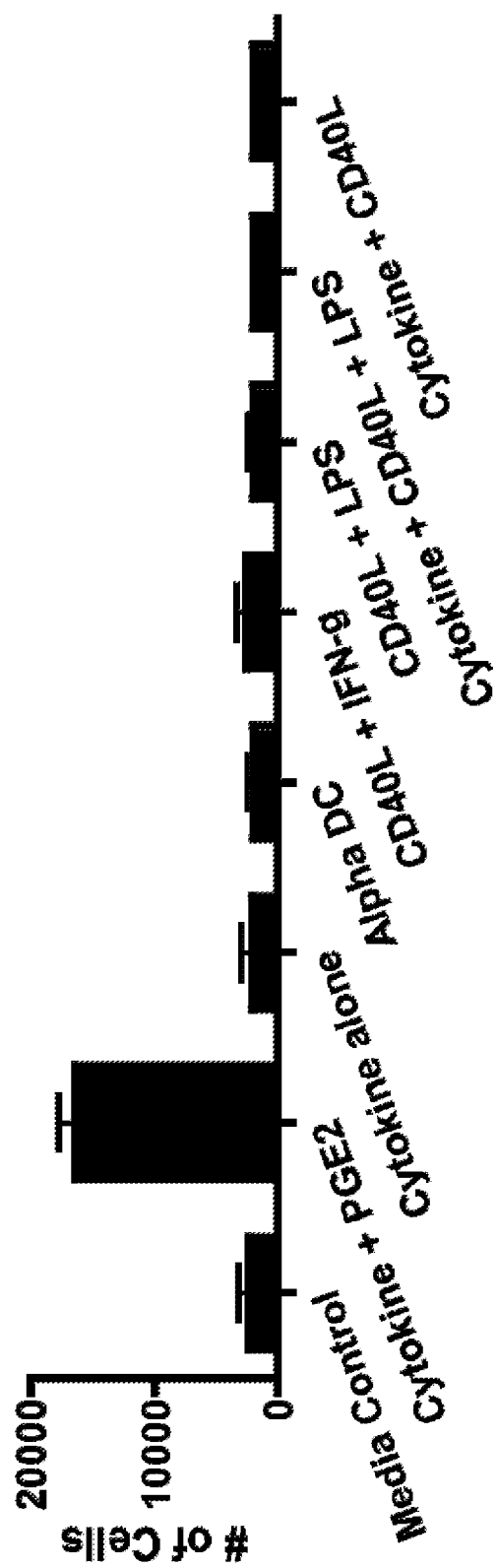
FIG. 2 is a graph showing migration of dendritic cells incubated in the presence of $PGE_2$ or alternative formulations that have been proposed to induce migration. Migration towards a mixture of lymph node chemokines CCL19 and CCL21 was measured.

As disclosed herein, human ex vivo generated dendritic cells electroporated with LMP1 and stimulated with recombinant cytokines IL-1β and TNFα efficiently migrated towards a mixture of lymph node chemokines CCL19 and CCL21. (FIG. 1). FIG. 1 depicts migration of DC electroporated with LMP1, LMP1-CD40, or control (eGFP)RNA in the presence or absence of cytokines or $PGE_2$. This migration can also be induced by $PGE_2$, but not by alternative immune stimulatory reagents. (FIG. 2). FIG. 2 depicts migration of DC incubated in the presence of $PGE_2$ or alternative formulations that have been proposed to induce migration. It is proposed that DC transfected with LMP1 and incubated with cytokines is able to induce IL-12p70 secretion after T cell help.

Molecular adjuvants enhance the cellular immune response. The term adjuvant includes agents that activate dendritic cells. The TNF superfamily of molecules such as CD40 ligand is one group of molecular adjuvant. (Kornbluth, R. S. and Stone, G. W. Immunostimulatory combinations: designing the next generation of vaccine adjuvants. J Leukoc Biol, 80(5): 1084-102 (2006)).

Progenitor cells transform into immature dendritic cells. Immature dendritic cells become activated after detecting an antigen that they can present on their cell surface. Immature dendritic cells degrade the antigen protein and present the fragments on their surface.

An immune response includes activation and maturation of dendritic cells. Dendritic cells are a part of the immune system that act as antigen-presenting cells. Dendritic cells process antigen material and present it on their cell surface using MHC molecules. Pattern recognition receptors, such as toll-like receptors (TLR), assist the dendritic cells in detecting viruses and bacteria. After a dendritic cell is activated, it migrates to the lymph nodes. Dendritic cells interact with other cells within the immune system such as T cells and B cells.

Stimulated dendritic cells produce IL-12. IL-12 helps naïve CD4+ T cells obtain a T helper cell type 1 (Th1) phenotype. Cytokines cause the development of T helper cell type 1 (Th1) and T helper cell type 2 (Th2) cells from naïve CD4+ T cells. The Th phenotypes each produce particular cytokines and can be identified by specific cell-surface markers.

CD40 is a membrane protein found on the surface of dendritic cells, among other types of cells, and is a member of the TNF receptor superfamily. CD40 binds to a ligand, CD40L, which is a glycoprotein and a member of the TNF superfamily. Dendritic cells upregulate cell surface receptors like CD80 and CD40.

As disclosed herein, LMP1, and potentially one or more LMP1 fusion proteins, is able to induce migration of transfected DC to the local draining lymph node at a level similar or superior to $PGE_2$. Prostaglandin $PGE_2$ induces the maturation of monocyte derived dendritic cells but may inhibit IL-12p70 by the dendritic cells. IL-12p70 is the biologically active form of IL-12. IL-12 is produced by activated dendritic cells and promotes the development of the Th1 phenotype. Il-12p70 is a heterodimer of IL-12p40 and IL-12p35. Therefore, LMP1 would be especially effective as a dendritic cell therapy reagent. Given that DC therapy often uses RNA encoding the antigen or immune stimulatory proteins for transfection, LMP1 can also be transfected as RNA. This is especially relevant for LMP1 because it is an oncogene. RNA is a safer method of transfection compared to DNA or viral vectors, given that RNA cannot integrate into the genome or be maintained. The RNA is degraded over time, and therefore LMP1 encoded as RNA would not persist in the patient after treatment.

The use of LMP1 and a LMP1-CD40 chimeric protein as vaccine adjuvants is disclosed herein. An LMP1-CD40 chimeric protein may include the transmembrane domain of LMP1 and the intracellular domain of CD40. LMP1 and LMP1-CD40 may be used as an adjuvant for a vaccine to increase an immune response to any antigen.

An immune response may be mounted to an antigen or antigens from any pathogen as a result of vaccination against that antigen or antigens. In one embodiment, the antigen may be derived from, but not limited to, pathogenic bacterial, fungal, or viral organisms, *Streptococcus* species, *Candida* species, *Brucella* species, *Salmonella* species, *Shigella* species, *Pseudomonas* species, *Bordetella* species, *Clostridium* species, Norwalk virus, *Bacillus anthracis, Mycobacterium tuberculosis*, human immunodeficiency virus (HIV), *Chlamydia* species, human Papillomaviruses, Influenza virus, *Paramyxovirus* species, Herpes virus, Cytomegalovirus, Varicella-Zoster virus, Epstein-Barr virus, Hepatitis viruses, *Plasmodium* species, *Trichomonas* species, sexually transmitted disease agents, viral encephalitis agents, protozoan disease agents, fungal disease agents, bacterial disease agents, cancer cells, or mixtures thereof.

A subject may be treated for an infectious pathogen or cancer. Examples of infectious pathogens include viruses such as, but not limited to, influenza, HIV, dengue virus, rotavirus, HPV, HBV, HCV, CMV, HSV, HZV, and EBV, pathogenic agents including the causative agents of Malaria, *Plasmodium(p)falciparum, P. malariae, P. ovale, P. vivax* and *P. knowlesi*; the causative agent of *Leishmania* (L), *L. major, L. tropica, L. aethiopica, L. mexicana, L. donovani, L. infantum syn. L. chagas*; and pathogenic bacteria including *Bacillus anthracis, Bordetella pertussis, Streptococcus pneumonia*, and *meningococcus*.

The vaccine may be used against any cancer or with any other therapy or intervention for cancer. Examples of cancers include HPV-induced cervical cancers (e.g., E7/E7 tumor associated antigens (TAA)), glioma, human melanoma (e.g., TRP-1, TRP-2, gp-100, MAGE-1, MAGE-3 and/or p53), breast cancer, and prostate cancer (e.g., TSA). Similarly for lung tumors, breast tumors, and leukemia, any suitable tumor associated antigen can be used, and many have been described. Many such TAA are common between various cancers (e.g., CEA, MUC-1, Her2, CD20).

This invention would solve the problem of properly activating and maturing dendritic cells for therapeutic vaccination of dendritic cells into patients as a treatment for cancer or chronic infections. More importantly, the invention would induce the migration of these DC from the site of injection to the draining lymph node. This invention may be used to treat cancer and chronic infections. This invention may also be used to develop prophylactic vaccines and other immune therapies dependent on immune activation and lymph node migration.

Disclosed herein is a different method to mature dendritic cells. Alternative technologies have been developed by individuals and companies that provide a mixture of cytokines and $PGE_2$ to mature dendritic cells and induce lymph node migration. The technology disclosed herein provides activation of the dendritic cells and leads to increased migration of the DC to the local draining lymph node while retaining the ability of these migrated DC to respond to T cell help by secreting IL-12p70.

Dendritic cell therapy or prophylactic vaccines targeting dendritic cells will induce activation and lymph node migration of the DC while presenting the antigen of interest to T cells in the lymph node and inducing T cell memory by secreting IL-12.

The methods disclosed herein are useful to induce the activation, migration, and IL-12 secretion by dendritic cells. Preliminary studies show that LMP1 is as effective as $PGE_2$, an inducer of dendritic cell migration. LMP1 combined with cytokines should be an equally effective method to induce migration of DC, while also being a superior method to induce IL-12 secretion by these same DC.

LMP1 transfection appears to mature DC with greater functional ability than the classic Mimic matured DC. Mimic is a composition comprising TNF-α, IL-1β, IL-6, and optionally $PGE_2$. After testing MDDC maturation protocols from the literature, the only protocols that yield DC with migratory ability are Mimic+$PGE_2$ and co-transfection of LMP1. Due to the increase in cytokine expression, 2-fold higher migration, and the increased number of Gag specific ELISpots, LMP1 appears to be a suitable replacement for the typical $PGE_2$ maturation.

The below described preferred embodiments illustrate adaptations of these compositions, kits, and methods. Nonetheless, from the description of these embodiments, other aspects of the invention can be made and/or practiced based on the description provided below.

Biological Methods

Methods involving conventional molecular biology techniques are described herein. Such techniques are generally known in the art and are described in detail in methodology treatises such as Molecular Cloning: A Laboratory Manual, 3rd ed., vol. 1-3, ed. Sambrook et al., Cold Spring Harbor Laboratory Press, Cold Spring Harbor, N.Y., (2001); and Current Protocols in Molecular Biology, ed. Ausubel et al., Greene Publishing and Wiley-Interscience, New York, (1992) (with periodic updates). Immunology techniques are generally known in the art and are described in detail in methodology treatises such as Current Protocols in Immunology, ed. Coligan et al., Greene Publishing and Wiley-Interscience, New York, (1992) (with periodic updates); Advances in Immunology, volume 93, ed. Frederick W. Alt, Academic Press, Burlington, Mass., (2007); Making and Using Antibodies: A Practical Handbook, eds. Gary C. Howard and Matthew R. Kaser, CRC Press, Boca Raton, Fla., (2006); Medical Immunology, 6th ed., edited by Gabriel Virella, Informa Healthcare Press, London, England, (2007); and Harlow and Lane ANTIBODIES: A Laboratory Manual, Cold Spring Harbor Laboratory Press, Cold Spring Harbor, N.Y., (1988).

Nucleic acid molecules encoding an antigen as described herein may be in the form of RNA (e.g., mRNA, microRNA, siRNA, shRNA or synthetic chemically modified RNA) or in the form of DNA (e.g., cDNA, genomic DNA, and synthetic DNA). The DNA may be double-stranded or single-stranded, and if single-stranded, may be the coding (sense) strand or non-coding (anti-sense) strand. In one embodiment, a nucleic acid can be an RNA molecule isolated or amplified from immortalized or primary tumor cell lines or dissected tumor tissue.

Typically, the subject is one who will receive a vaccine, or for whom vaccine administration is being considered.

Any suitable biological sample can be tested for immune response. Examples of biological samples include blood, serum, plasma. The sample may be tested using any suitable protocol or assay. Examples of suitable assays include enzyme-linked immunosorbent assays (ELISAs), Western blots, flow cytometry assays, immunofluorescence assays, qPCR, microarray analysis, etc.

In an embodiment, an antibody (e.g., monoclonal, polyclonal, Fab fragment, etc.) specific for a given protein may be used. In some embodiments, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the kits, assays and methods described herein. A kit may contain antibodies and other components, packaging, instructions, or other material to aid in the use of the kit.

Described herein are kits for activating dendritic cells and for preparing a vaccine formulation. A typical kit for activating dendritic cells as described herein may be, in one embodiment, include LMP1 and optionally at least one cytokine A kit may include a well plate to carry the mixture of the different reagents, as well as one or more washing buffers. Optionally, kits may also contain one or more of the following: containers which include positive controls, containers which include negative controls, photographs or images of representative examples of positive results and photographs or images of representative examples of negative results.

Effective Doses

The compositions described above are preferably administered to a mammal (e.g., non-human primate, bovine, canine, rodent, human) in an effective amount, that is, an amount capable of producing a desirable result in a treated subject (e.g., delaying or preventing onset of a disease or disorder in the subject). Toxicity and therapeutic efficacy of the compositions utilized in methods described herein can be determined by standard pharmaceutical procedures. As is well known in the medical and veterinary arts, dosage for any one animal depends on many factors, including the subject's size, body surface area, age, the particular composition to be administered, time and route of administration, general health, and other drugs being administered concurrently.

The amount of the therapeutic agent to be administered varies depending upon the manner of administration, the age and body weight of the patient, and with the pathology of the disease. A composition as described herein is typically administered at a dosage that activates and matures dendritic cells, as assayed by identifying levels of dendritic cell migration or using any that assay that measures activation or maturation of dendritic cells, such as IL-1α, IL-1β, IFN-α, IFN-β, IFN-γ, IL-2, IL-4, IL-6, IL-1β, IL-12, IL-15, IL-16, IL-17, IL-18, TNF-alpha. In one embodiment, the assay measures activation or maturation of denditric cells by measuring IFN-γ or IL-2 secretion.

Therapeutic compositions described herein can be administered to a subject by any suitable delivery vehicle and route. The administration of a composition may include a therapeutically effective amount of a vaccine formulation. The composition may be provided in a dosage form that is suitable for local or systemic administration (e.g., parenterally, subcutaneously, intravenously, intramuscularly, intraperitoneally, intracranially). In various embodiments, the composition may be provided in a dosage form that is suitable for oral administration or intranasal administration. The pharmaceutical compositions may be formulated according to conventional pharmaceutical practice (see, e.g., Remington: The Science and Practice of Pharmacy (20th ed.), ed. A. R. Gennaro, Lippincott Williams & Wilkins, (2000) and Encyclopedia of Pharmaceutical Technology, eds. J. Swarbrick and J. C. Boylan, Marcel Dekker, New York (1988-1999)).

Compositions as described herein may be administered parenterally by injection, infusion or implantation (subcutaneous, intravenous, intramuscular, intraperitoneal, or the like) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation. Formulations can be found in Remington: The Science and Practice of Pharmacy, supra.

Compositions for parenteral use may be provided in unit dosage forms (e.g., in single-dose ampoules), or in vials containing several doses and in which a suitable preservative may be added. The composition may be in the form of a solution, a suspension, an emulsion, an infusion device, or a delivery device for implantation, or it may be presented as a dry powder to be reconstituted with water or another suitable vehicle before use. Apart from the agent that activates and matures dendritic cells, the composition may include suitable parenterally acceptable carriers and/or excipients. The active therapeutic agent(s) may be incorporated into microspheres, microcapsules, nanoparticles, liposomes, or the like for controlled release. Furthermore, the composition may include suspending, solubilizing, stabilizing, pH-adjusting agents, tonicity adjusting agents, and/or dispersing agents.

As indicated above, the pharmaceutical compositions described herein may be in a form suitable for sterile injection. To prepare such a composition, the suitable active therapeutic(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution and dextrose solution. The aqueous formulation may also contain one or more preservatives (e.g., methyl, ethyl or n-propyl p-hydroxybenzoate). In cases where one of the compounds is only sparingly or slightly soluble in water, a dissolution enhancing or solubilizing agent can be added, or the solvent may include 10-60% w/w of propylene glycol or the like.

Materials for use in the preparation of microspheres and/or microcapsules are, e.g., biodegradable/bioerodible polymers such as polygalactin, poly-(isobutyl cyanoacrylate), poly(2-hydroxyethyl-L-glutam-nine) and, poly(lactic acid). Biocompatible carriers that may be used when formulating a controlled release parenteral formulation are carbohydrates (e.g., dextrans), proteins (e.g., albumin), lipoproteins, or antibodies. Materials for use in implants can be non-biodegradable (e.g., polydimethyl siloxane) or biodegradable (e.g., poly(caprolactone), poly(lactic acid), poly(glycolic acid) or poly(ortho esters) or combinations thereof).

LMP1 and at least one cytokine may be mixed together in a single composition, or may be administered separately. For example, the LMP1 may be administered in combination with any other standard dendritic cell therapy; such methods are known to the skilled artisan and described in Remington's Pharmaceutical Sciences by E. W. Martin. Formulations for oral use include a liquid containing the active ingredient(s) (e.g., LMP1 and at least one cytokine) in a mixture with non-toxic pharmaceutically acceptable excipients.

EXAMPLES

The present invention is further illustrated by the following specific examples. The examples are provided for illustration only and should not be construed as limiting the scope of the invention in any way.

Example 1

Human Monocyte Isolation

PBMC were isolated from human buffy coats. Human buffy coats were purchased from Continental Blood Bank (Miami, Fla.). Buffy coats were ficolled (GE Healthcare Ficoll) and the peripheral blood mononuclear cell (PBMC) layer was washed with warm PBS three times at decreasing speeds: 1800 rpm, 1100 rpm, and 1000 rpm. The PBMCs were plated in a T175 flask at a concentration in 40 mL of pre-warmed human DC media (RPMI1640 (Hyclone), 5% human AB serum male only (Lonza), PenStrep (1×), and Hepes) Flasks were incubated for 2 hours at 37° C. in 5% $CO_2$ after which all non-adherant cells were washed away with human DC media.

Monocyte Derived Dendritic Cell Preparation

Isolated monocytes were cultured for 5 days in human DC media supplemented with GM-CSF, 1000 U/mL (BERLEX Inc.), and IL-4, 500 U/mL (R&D systems. To harvest imma-ture DC, flasks were placed at 4° C. for 30 minutes. Non-adherent and semi-adherent dendritic cells were collected by washing the flasks three times with cold PBS. Remaining adherent cells were discarded.

Transwell® Migration

Immature dendritic cells were resuspended in human DC media and matured using various protocols using Mimic cytokine mix (5 ng/mL of TNF-α [R&D], 5 ng/mL of IL-1β [R&D], 750 ng/mL of IL-6 [R&D], and 1 μg/mL of $PGE_2$ [Sigma]), Mega-CD40L™ (Enzo Life Sciences), and LPS. MegaCD40L™ contains two trimeric CD40 ligands linked by the collagen domain of ACRP30/adiponectin. Cells were cultured for 36 hours at 37° C. in 5% $CO_2$, 150,000 mature dendritic cells in 100 μL were added to 8 μm Transwell® supports (Greiner Bio-one) in triplicate. Transwell® were put into a 24 well plate with 600 μL of human dendritic cell media and 150 ng/mL of CCL19 (Peprotech). After 90 minutes incubation at 37° C., Transwell® were removed and all dendritic cells in the lower chamber, removed with EDTA, and counted.

Flow Cytometric Analysis

Mature dendritic cells were harvested and washed once with FACS buffer (PBS+1% human AB serum+0.1% sodium azide). Cells were then blocked with blocking buffer (PBS+ 20% human AB serum) for 30 minutes at 4° C. Blocked cells were washed an addition time with FACS buffer and stained. FcR blocking reagent (Miltenyi Biotec) was added to all samples as an additional blocking step. Surface CCR7 was stained using Anti-CCR7PE-Cy7 (BD Bioscience). Stained samples were run on a LSR-Fortessa (BD Bioscience).

mRNA Preparation and Dendritic Cell Transfection

Sequences encoding pLyso-Gag, LMP1, and LMP1-CD40 were cloned into the pGEM4z plasmid containing a T7 promoter and a 64 base pair polyA tail (pGEM4Z/A64). pGEM4Z containing GFP (provided by Eli Gilboa) was used as a control in all human transfection experiments. Ambion mMESSAGE mMACHINE RNA in vitro transcription kit was used for in vitro mRNA synthesis.

Five day immature dendritic cells were harvested and washed two times with Opti-MEM medium (GIBCO). Cells were resuspended in Opti-MEM at a concentration of $1 \times 10^7$ mL. 200 μL of cells was mixed with 10 μg of RNA and transfected in a pre-chilled 0.4 cm electroporation cuvette (Bio-Rad). A Bio-Rad Gene Pulser X cell Electroporator was used to electroporate the dendritic cells at 350 V and 150 μF. Post electroporation, DC were cultured in 6-well plates in the presence of GM-CSF and IL-4 and maturation cocktails where indicated. After 48 hours, migration was tested by Transwell® migration assay as described herein.

Preparation of Mouse Bone Marrow-Derived DC

Bone marrow was harvested from the femurs of 6-7 week old Balb/c mice by flushing each bone shaft with cold PBS. The PBS marrow solution was then strained using a 70 μm cell strainer. Any large marrow pieces were homogenized using the plunger of a 3 mL syringe. Cells were washed twice with PBS and resuspended at a concentration of $1 \times 10^6$ cell/mL in R10 media (RPMI1640+10% FBS) containing 20 ng/mL murine GM-CSF (Peprotech) and 10 ng/mL of murine IL-4 (Peprotech). Cells were plated in 6 well plates and incubated from 5 days at 37° C. in 5% $CO_2$ (day 0). On day 3, media was changed and 3 mL of fresh complete R10 medium containing GM-CSF and IL-4 were added. On day 5, the non-adherent cells were collected by washing three times with cold PBS.

Bone Marrow Derived Dendritic Cell (BMDDC) Transfection

The immature dendritic cells removed from the 6 well plate and washed twice with Opti-MEM medium and resuspended in Opti-MEM at a concentration of $1 \times 10^7$ cells/mL. Dendritic cells were mixed with 10 μg of RNA and were electroporated in a chilled 0.4 cm electroporation cuvette at 350 V and 150 μF. After transfection, cells were replated in R10 media containing GM-CSF and IL-4 and maturation cocktails where indicated.

CFSE Labeling

On day 7 (untransfected) or 48 hours after electroporation, non adherent and loosely adherent cells were harvested. The cells were resuspended in a 15 mL tube in a 1 mL volume of PBS containing 5% FBS. 110 µL of PBS was added horizontally as a droplet to the non-wetted portion of the tube. 1.1 µL of 5 mM CFSE was added to this droplet, and the tube was immediately capped, inverted, and vortexed. After thorough mixing, tubes were incubated in the dark for 5 minutes at room temperature. The cells were then quenched with ten volumes of cold R10 media and kept in ice for 5 minutes. Labeled cells were washed twice with cold R10 media and followed by two additional washes with PBS.

In Vivo Migration Assay

The CFSE-labeled cells were injected intradermally into the thighs of Balb/c mice (1-4 million cells injected per mouse). The no treatment mouse was injected with identical volumes of PBS. After 48 hours, inguinal lymph nodes was harvested. Lymph node were cut into pieces and incubated for 25 minutes with Collagenase Type II (200 U/mL) and 200 U/mL DNase. EDTA was then added to 0.01 M and incubated for an additional 5 minutes. The lymph node was then ground through a 70 µm cell strainer and washed thoroughly. The cells were spun down, transferred to FACS tubes, fixed using 2% formalin, and run on an LSR-Fortessa (BD Bioscience) to obtain an accurate number of successfully migrated CFSE labeled dendritic cells.

DC Maturation Protocols

Immature dendritic cells were resuspended in human DC media and matured using various protocols including Mimic, Alpha, and Von Gool. The protocols are as follows: (1) Mimic matured cytokine mix (5 ng/mL of TNF-α [R&D)], 5 ng/mL of IL-1β [R&D], 750 ng/mL of IL-6 [R&D], and 1 µg/mL of $PGE_2$ [Sigma]), (2) Alpha DC cytokine mix (3000 U/ml TNF-α, 1000 U/ml IFN-γ, and 20 µg/ml polyinosinic:polycytidylic acid (Poly I:C)), or (3) Von Gool DC cytokine mix (2000 U/ml IL-1β and 1000 U/ml TNF-α). The cells were cultured for 36 hours at 37° C. in 5% $CO_2$ and then used for migration assays.

Example 2

Figure 3:
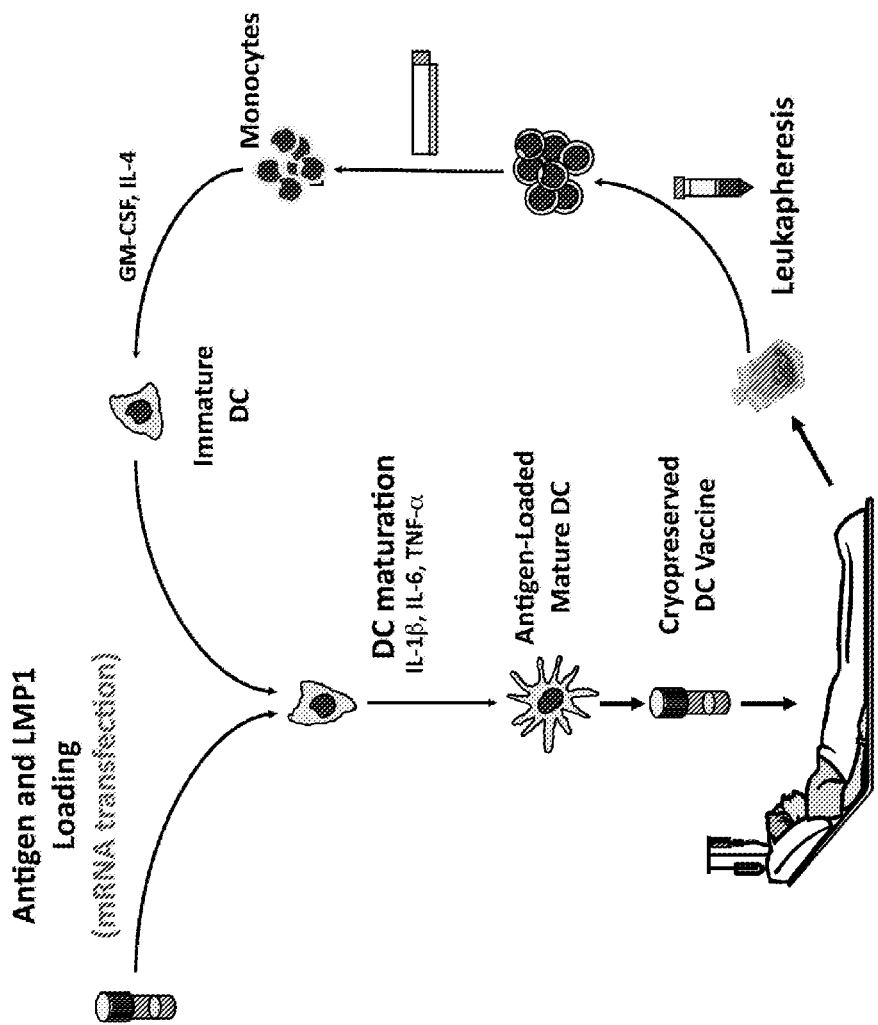
FIG. 3 is a schematic illustration of vaccine design.

Disclosed herein is a method to mature dendritic cells that retain functional and migratory abilities without the side effects that result from maturing the dendritic cells using $PGE_2$. FIG. 3 is a schematic illustration of vaccine design. The DC may be matured using LMP1 or LMP1-CD40 and optionally at least one cytokine instead of Mimic.

Vaccines were prepared by the following method. Monocytes are removed from the patients and matured into immature dendritic cells using GM-CSF and IL-4. The immature DC are electroporated with antigen mRNA and matured with Mimic. Mimic is a composition comprising TNF-α, IL-1β, IL-6, and $PGE_2$. Specifically, the Mimic cytokine mix may be comprised of 5 ng/ml TNFα, 5 ng/ml IL-1β, 750 ng/ml IL-6 and 1 µg/ml $PGE_2$. The DC were cultured overnight at 37° C. in 5% $CO_2$. Matured DC that are expressing antigen are cryopreserved and readministered to the patient over the course of their treatment. (FIG. 3).

Molecular adjuvants were transfected as mRNA along with HIV Gag mRNA by electroporation. After 48 hours of maturation, supernatants were collected and measured for cytokine levels by cytometric bead array. Maturation and activation markers were analyzed by cell surface staining and flow cytometric analysis. Mature antigen loaded DC were cultured with PBL for 12 days followed by re-stimulation with 10 µg/ml Gag peptide and ELISpot for IFN-γ and IL-2. DC migratory ability was tested by Transwell® migration assay in response to CCL19.

Example 3

Referring to FIGS. 4A-4E, immature dendritic cells were transfected with 10 µg construct RNA and cultured for 48 hours. DC were then stained and analyzed by flow cytometry.

LMP1 and LMP1-CD40 significantly increase markers of maturation and activation including CCR7, CD86, CD83, CD80, and CD40. (FIGS. 4A-4E). LMP1-CD40 consists of the LMP1 transmembrane domain and the CD40 cytoplasmic tail domain. The N-terminal residues of LMP1 form six transmembrane regions. The cytoplasmic tail contains signaling domains.

Figures 4A, 4B:
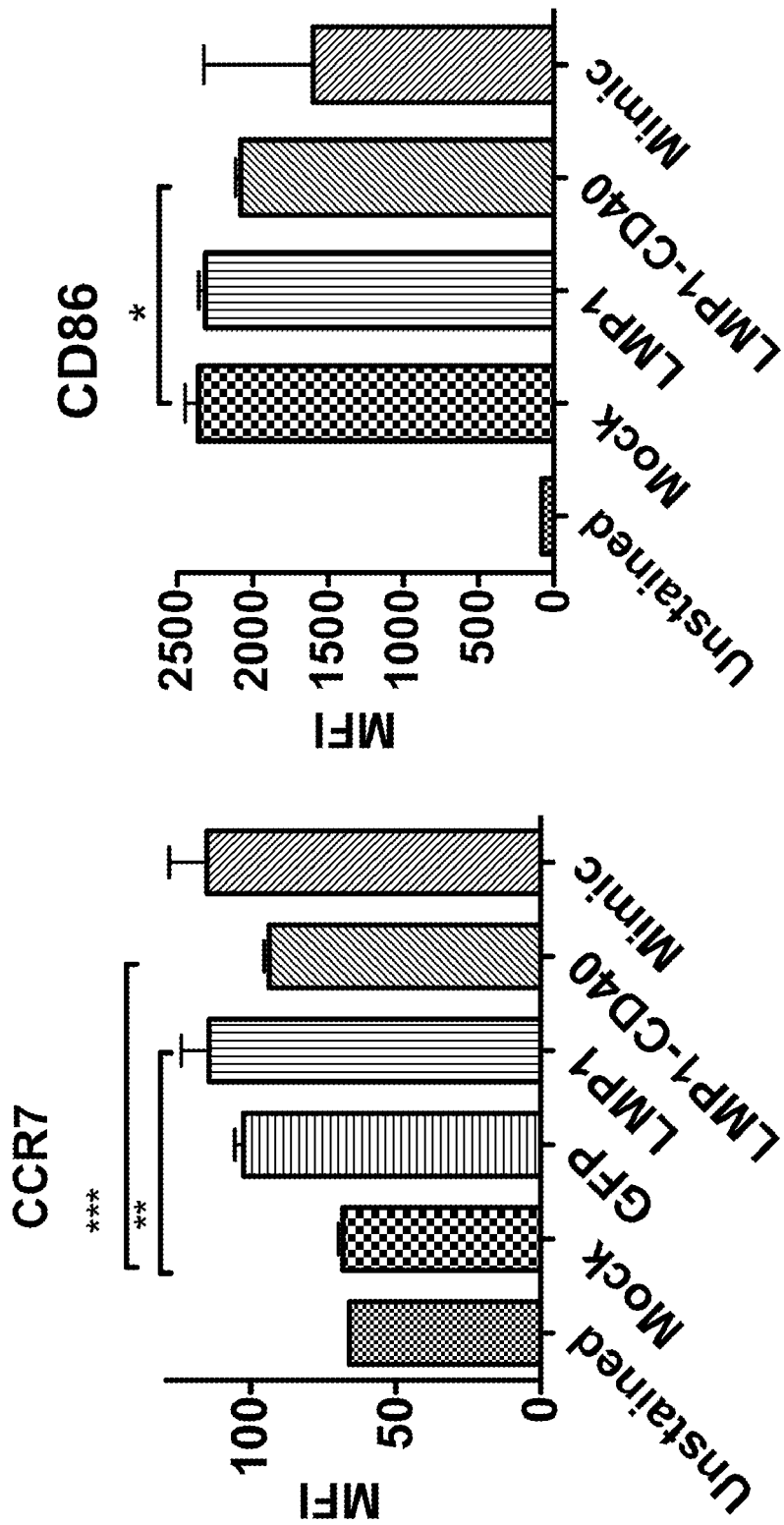
FIGS. 4A-4E show the mean fluorescence intensity (MFI) of immature dendritic cells that were transfected with construct RNA, cultured for 48 hours, stained, and analyzed by flow cytometry. Markers of maturation and activation including CCR7, CD86, CD83, CD80, and CD40 were measured.
Figure 4D:
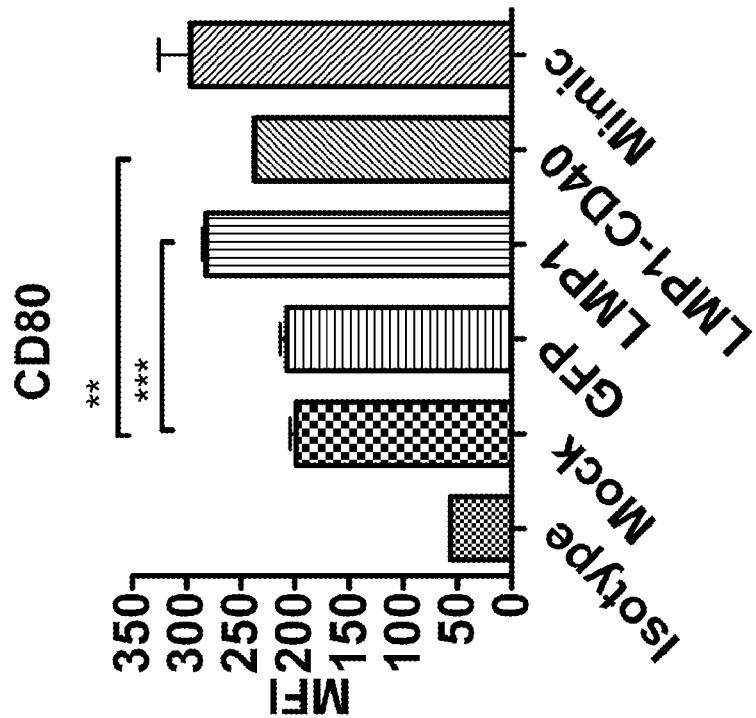
Figure 4C:
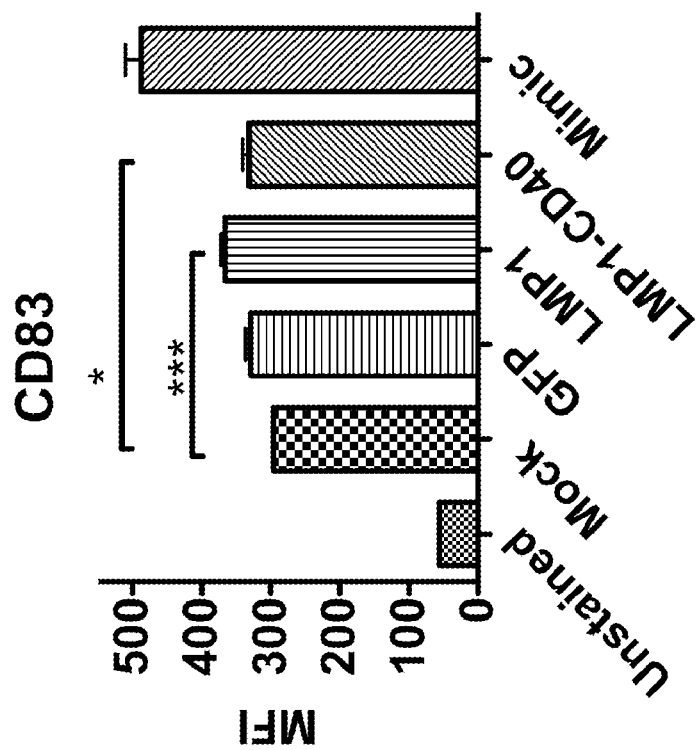
Figure 4E:
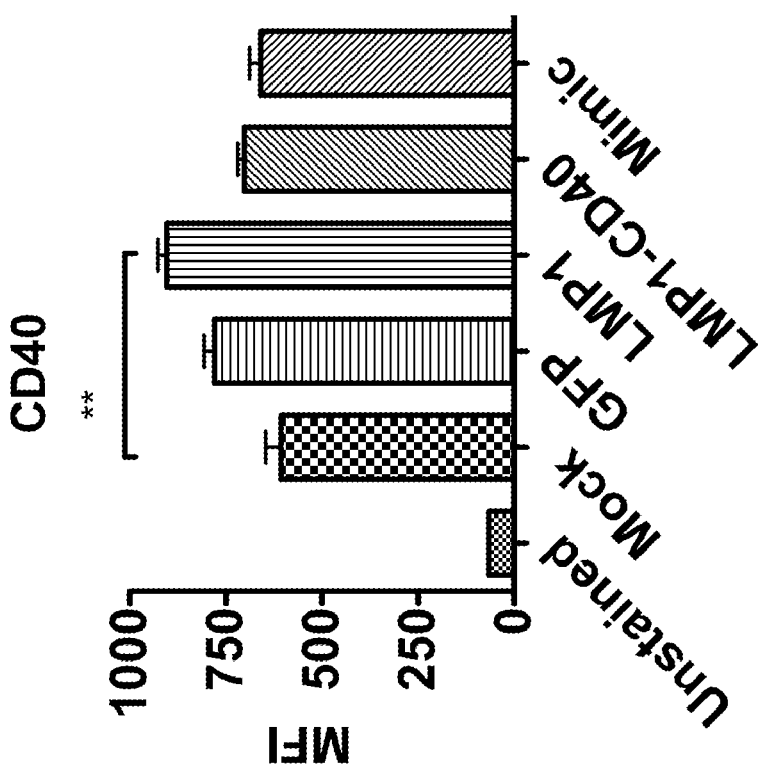

CCR7 is upregulated to levels comparable to those of Mimic matured DC, which suggests that the DC may be able to migrate to the draining lymph node. (FIG. 4A).

Example 4

Referring to FIGS. 5A-5F, supernatant samples were collected 48 hours after transfection and analyzed using the BD Human Inflammatory Cytokine Kit. The BD Human Inflammatory Cytokine Kit can be used to quantitatively measure interleukin-8 (IL-8), interleukin-β (IL-β), interleukin-6 (IL-6), interleukin-1β (IL-1β), tumor necrosis factor (TNF), and interleukin-12p70 (IL-12p70) protein levels. (BD Cytometric Bead Array (CBA) Human Inflammatory Cytokines Kit Instruction Manual, Becton, Dickinson, and Company, (2010). The kit includes beads of known size and fluorescence that capture a particular analyte so that the presence of the analyte can be detected using flow cytometry. The phycoerythrin (PE)-conjugated antibodies present in the kit act as a detection reagent with a fluorescent signal proportional to the amount of bound analyte.

Figures 5A, 5B:
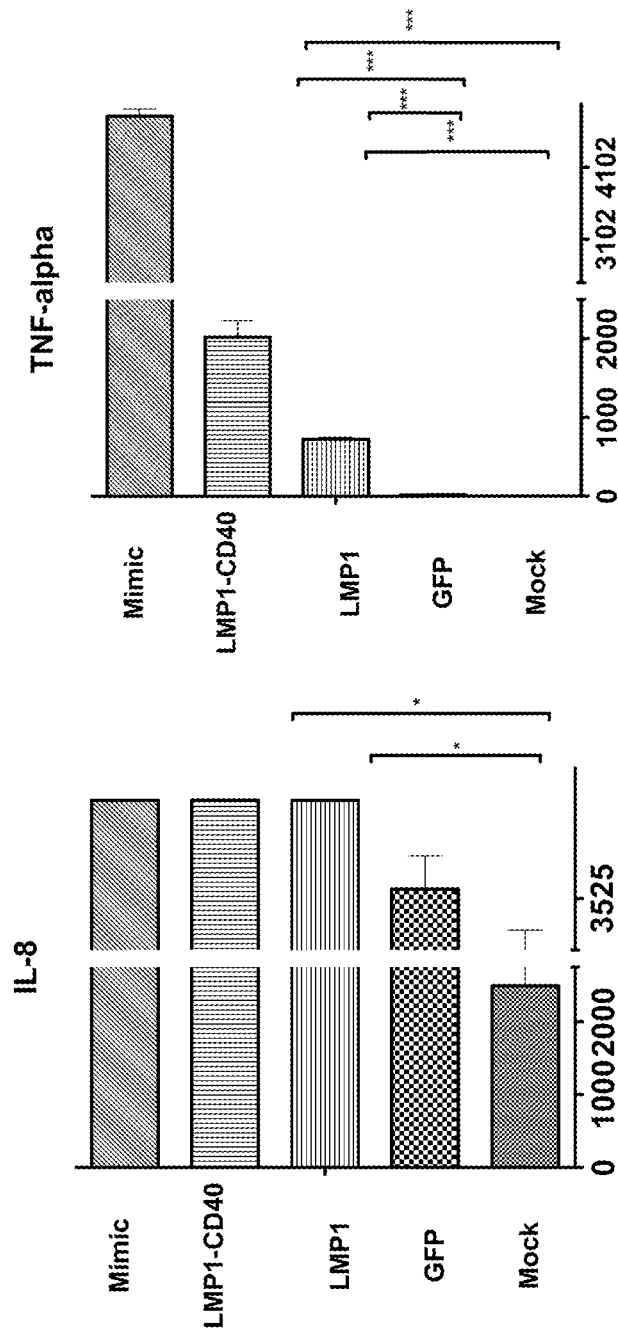
FIGS. 5A-5F show the results of analysis of supernatant samples that were collected 48 hours after transfection and analyzed using the BD Human Inflammatory Cytokine Kit. The levels of various inflammatory cytokines were measured.
Figures 5C, 5D:
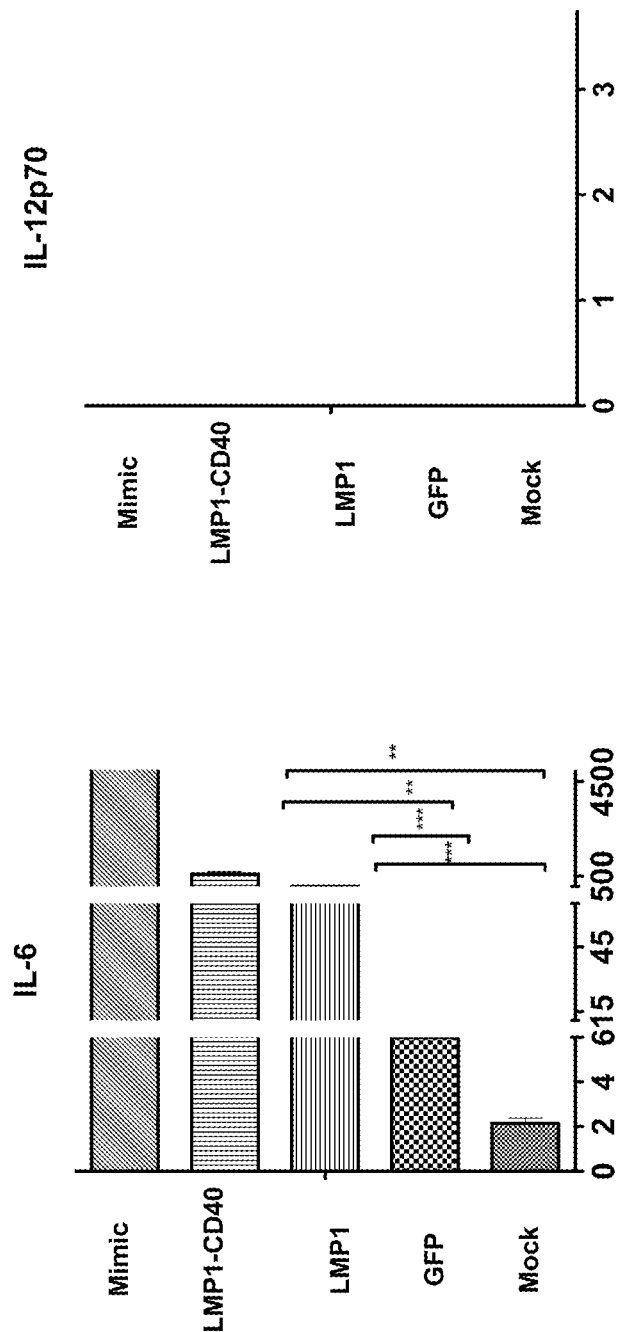
Figure 5F:
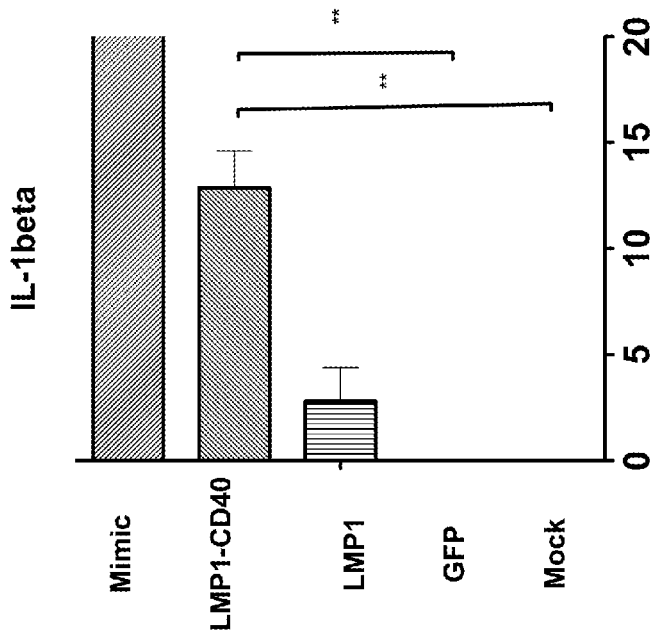
Figure 5E:
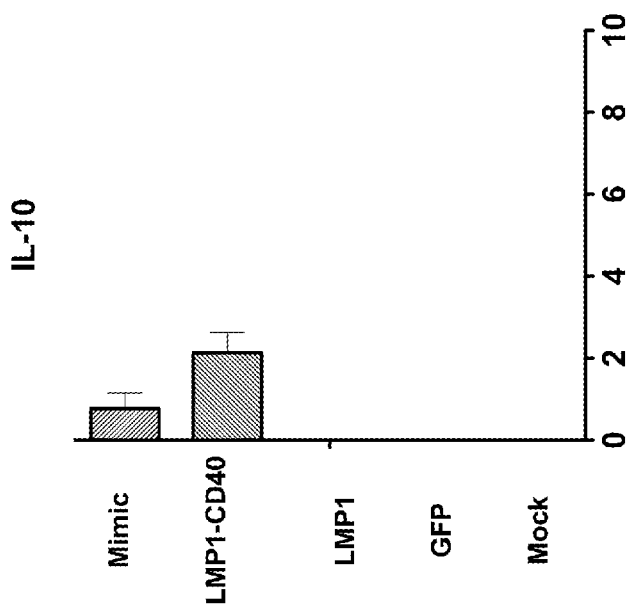

LMP1 and LMP1-CD40 significantly up-regulate the expression of inflammatory cytokines (FIGS. 5A-5F). The cytokine profile appears to mirror what is seen for Mimic DC. Expression of IL-12p70 in the culture supernatant was not detected. (FIG. 5D).

Example 5

Figure 6:
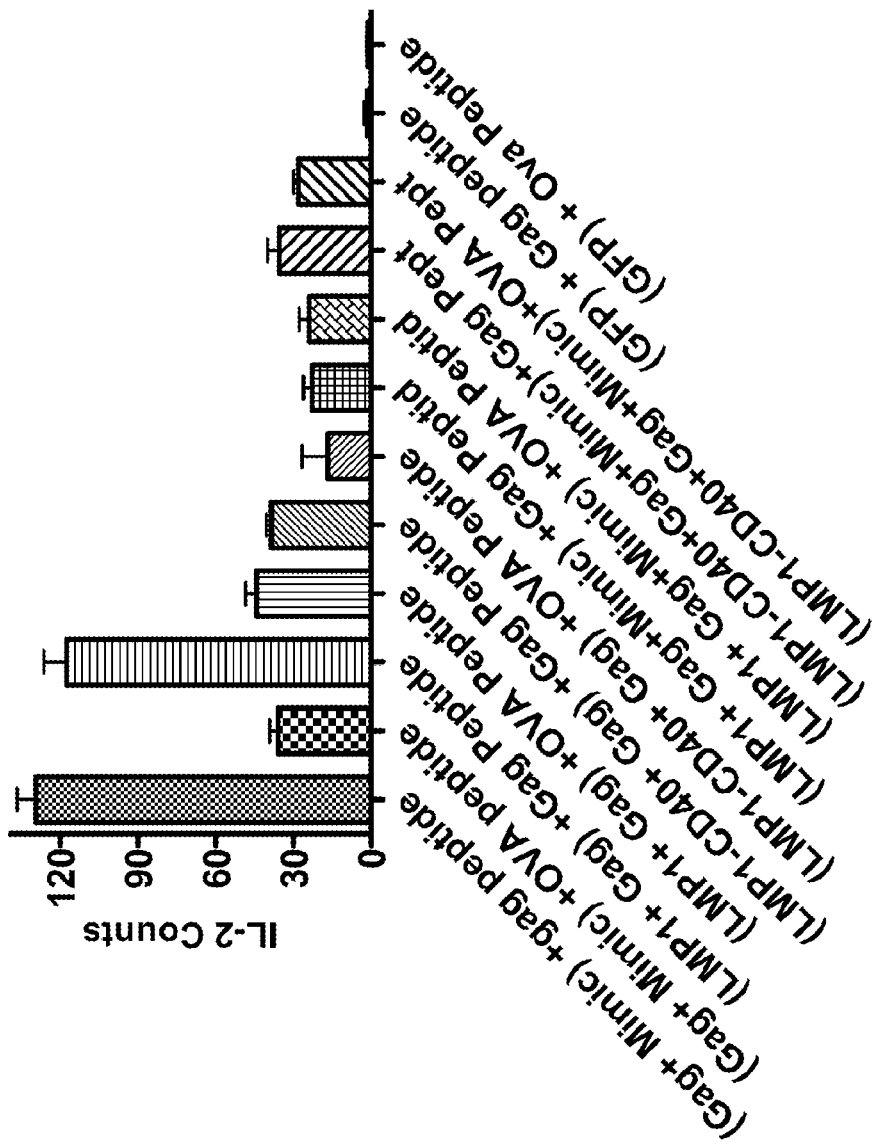
FIG. 6 shows the IL-2 counts measured by an enzyme-linked immunosorbent spot (ELISpot) assay for DC cultured with peripheral blood leukocytes (PBL) and then restimulated with Gag or Ova peptide.

Referring to FIG. 6, DC were cultured with PBL for 12 days. On day 12, the DC were restimulated with Gag or Ovalbumin (Ova) peptide and measured for IFN-γ and IL-2 secretion by an enzyme-linked immunosorbent spot (ELISpot) assay. The Gag and Ova peptides act as antigens. Gag peptides may be used to determine if matured DC loaded with Gag peptides are able to induce Gag specific IFN-γ and IL-2 responses. Ova peptides are used for the study of CD4 T cell response. Class II MHC binds the Ova peptides and presents them to T cells.

The results of the IFN-γ and IL-2 ELISpot assays show a significant increase in the ability of DCs to present antigen and activate T cells when co-transfected with LMP1. (FIG. 6). Levels were similar to those for DCs matured by Mimic.

Example 6

Figure 7:
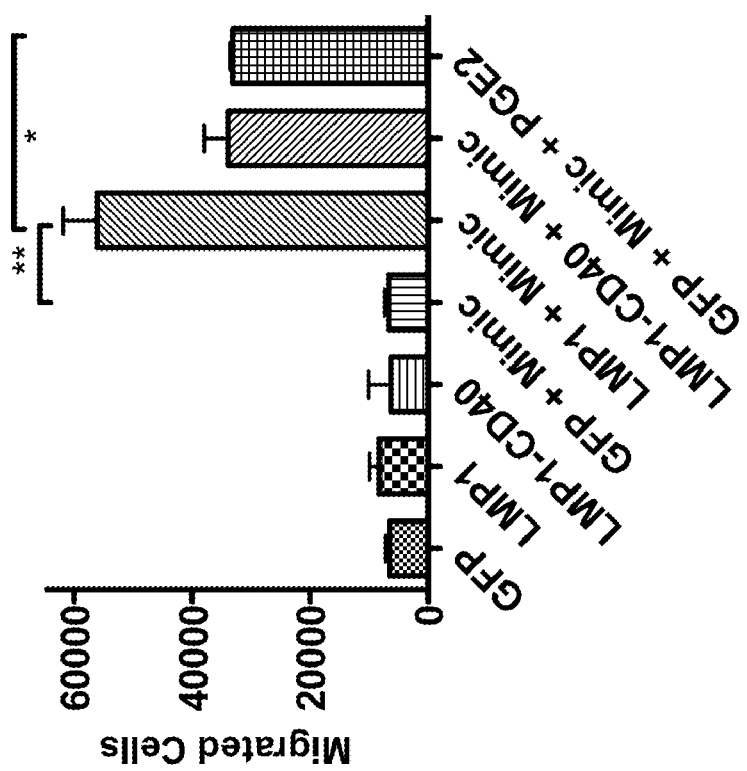
FIG. 7 shows the percent migration for DC added to the top well of a Transwell® support and allowed 90 minutes to migrate towards CCL19. The Transwell® was then removed and all cells in the lower chamber were counted.

Referring to FIG. 7, 150,000 DC were added to the top well of a permeable support (in this example, a Transwell® permeable support). The DC were allowed 90 minutes to migrate towards CCL19 after which the Transwell® was removed and all cells in the lower chamber were counted. CCL19 is a chemokine that attracts dendritic cells and binds to the CCR7 receptor.

LMP1 and LMP1-CD40 alone failed to mature DC capable of migration. (FIG. 7). LMP1 transfected DC cultured in the presence of Mimic without $PGE_2$ showed 2-fold higher migratory abilities than Mimic matured DC+$PGE_2$. LMP1-CD40 transfected DC in the presence of Mimic migrate as well as $PGE_2$ matured DC.

Example 7

Referring to FIG. 8A-8D, in vivo migration of DC can be measured in mice injected intradermally (i.d.) with carboxyfluorescein succinimidyl ester (CFSE)-labeled DC. CFSE is a fluorescent dye that can be used to label lymphocytes and track their migration in vivo. A million bone marrow derived BALB/c DC were labeled with CFSE and injected i.d. into the flank of mice. After 24 hours, the draining inguinal lymph node was dissected and measured for CFSE.

Figures 8A, 8B, 8C, 8D:
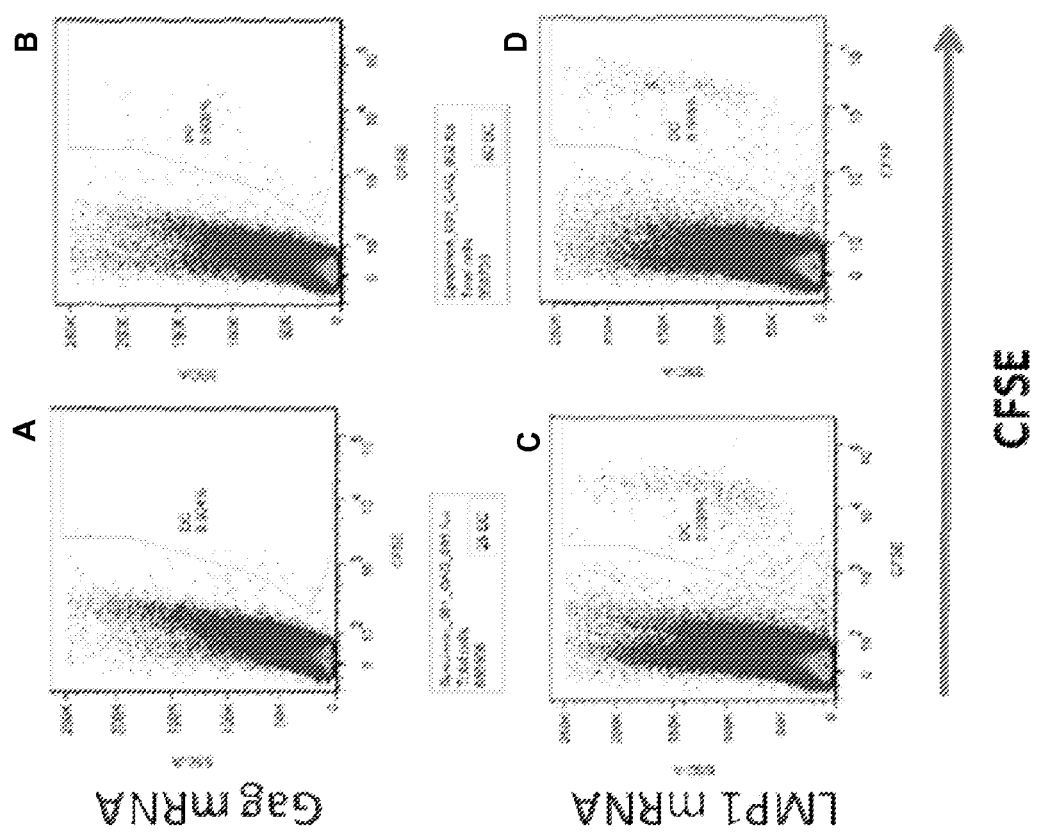
(FIGS. 8A and 8B).

LMP1 mRNA transfected DC (FIGS. 8C and 8D) were able to migrate and were detected as a distinct CFSE+ population. Control Gag treated DC did not migrate. (FIGS. 8A and 8B).

Example 8

Figures 9A, 9B:
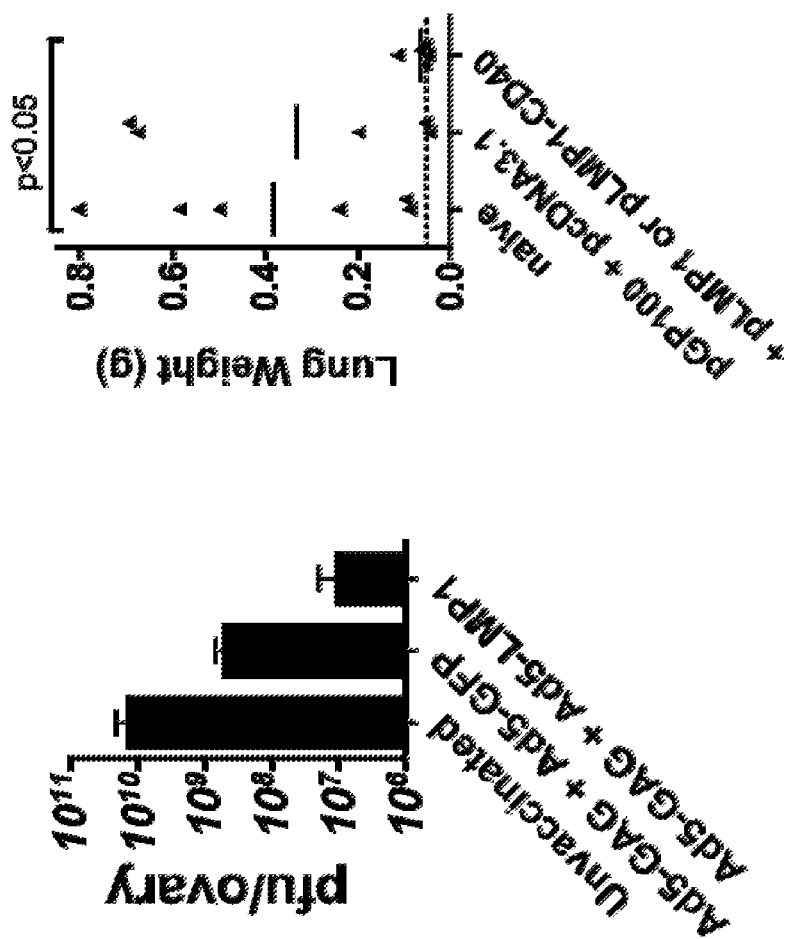
FIG. 9A shows ovary viral load 5 days after mice were vaccinated with Ad5 adenoviral vector vaccines, such as Ad5-Gag+Ad5LMP1, intramuscularly (i.m.) twice at 2 week intervals and challenged two weeks later.
FIG. 9B shows lung weights after mice were vaccinated with a DNA vaccine encoding human gp100 (i.m. every 2 weeks×3) and challenged intravenously (i.v.) with B16-F10 cells and then sacrificed on day 22 post challenge. Lung weights were compared between gp100+empty vector and gp100+LMP1 or LMP1-CD40 adjuvant (4 mice in total). The dashed line is normal lung weight.

Referring to FIG. 9, pilot studies were performed evaluating LMP1 and LMP1-CD40 as vaccine adjuvants. In FIG. 9A, Ad5 adenoviral vector vaccines combining Ad5-Gag+Ad5-LMP1 induced a 1-2 log decrease in vaccinia-Gag viral load after murine challenge when compared to Ad5-Gag+Ad5-GFP control virus. Mice were vaccinated intramuscularly (i.m.) twice at 2 week intervals, then challenged two weeks later. Ovary viral load was measured 5 days later.

In FIG. 9B, mice vaccinated with a DNA vaccine encoding human gp100 (i.m. every 2 weeks×3) were challenged intravenously (i.v.) with B16-F10 cells and then sacrificed on day 22 post challenge. Lung weights were compared between gp100+empty vector and gp100+LMP1 or LMP1-CD40 adjuvant (4 mice in total). All lungs with increased weight had visible tumors. The dashed line is normal lung weight.

Example 9

Figure 10:
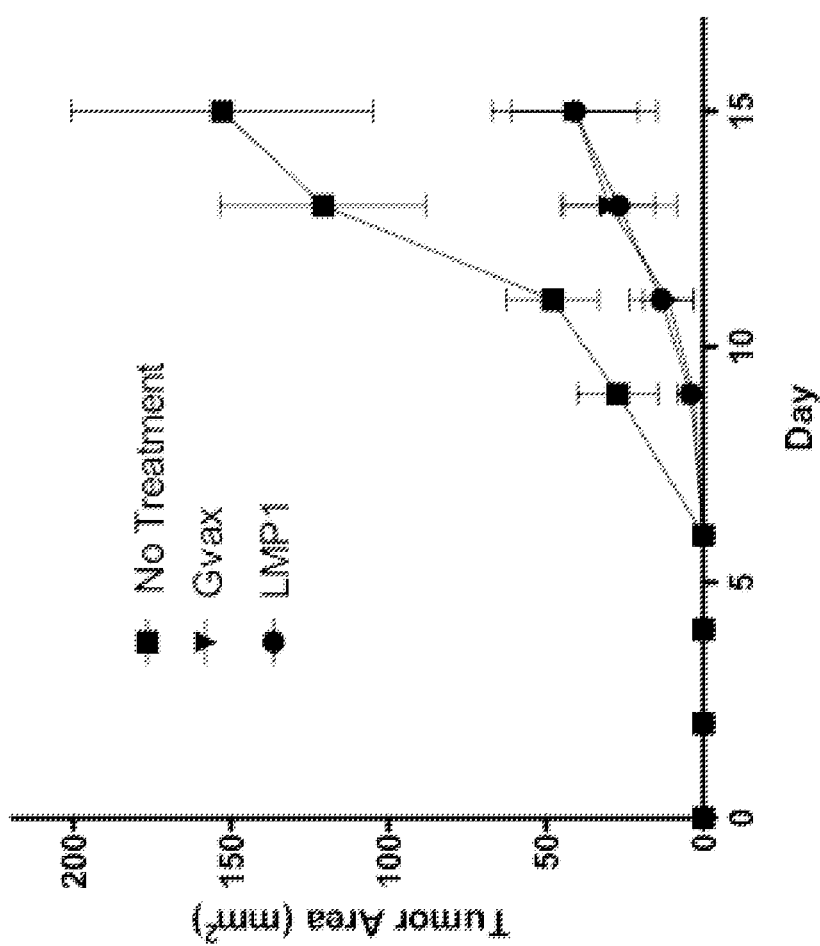
FIG. 10 shows tumor area following cell therapy with LMP1-transfected dendritic cells. Mice were challenged with 50,000 B16-F10 cells by intradermal (i.d.) injection in the flank. Mice were either left untreated, injected i.d. with irradiated GVAX cells (B16 cells expressing GM-CSF), or injected i.d. in the footpad with bone marrow derived dendritic cells transfected with LMP1 mRNA.

Referring to FIG. 10, cell therapy with LMP1-transfected dendritic cells reduce tumor growth in C57BL/6 tumor bearing mice at a similar level to the cancer therapy GVAX.

Mice were challenged with 50,000 B16-F10 cells by intradermal (i.d.) injection in the flank. Mice were either left untreated, injected i.d. with irradiated GVAX cells (B16 cells expressing GM-CSF), or injected i.d. in the footpad with bone marrow derived dendritic cells transfected with LMP1 mRNA.

Example 10

Figures 11A, 11B, 11C:
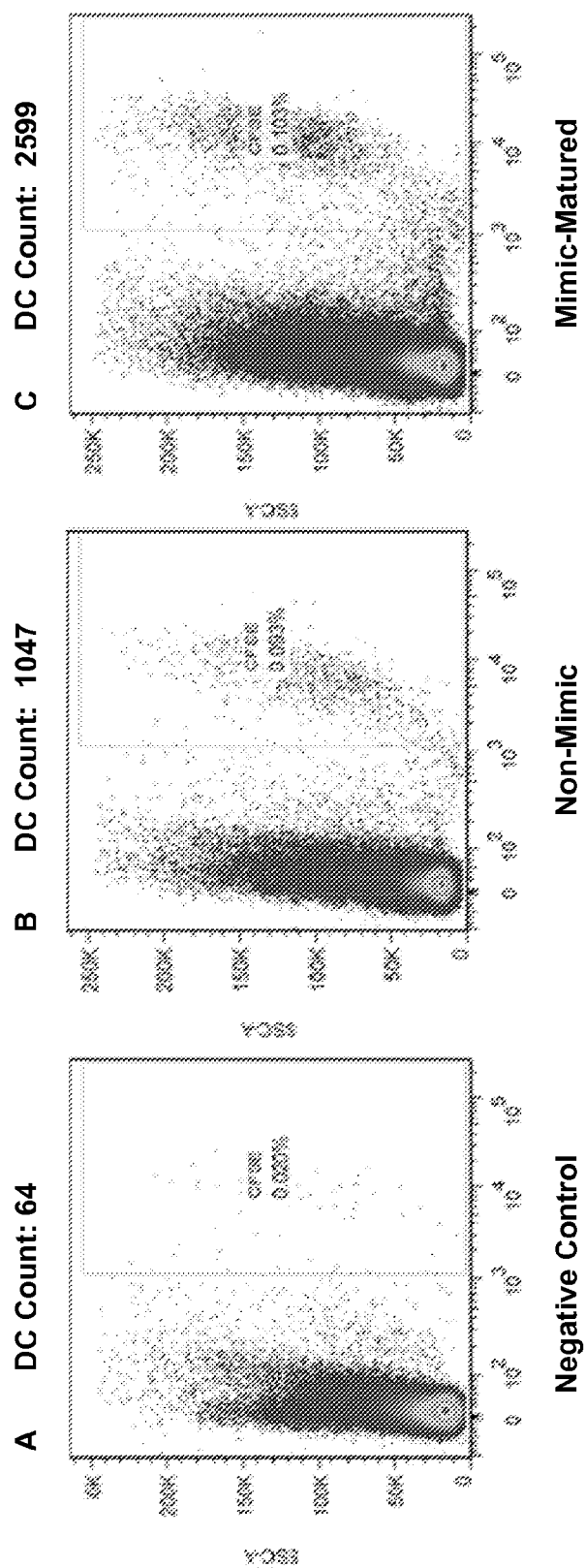
FIG. 11 shows measurement of DC migration in vivo in Balb/c mice. Bone-marrow derived DC were generated by a five day culture with mGM-CSF and mIL-4. Cells were harvested and put into culture with the Mimic cytokine cocktail (FIG. 11C) or electroporated with 10 μg Gag (FIGS. 11F and 11G) or LMP1 mRNA (FIGS. 11H and 11I). After 36 hours of maturation, cells were washed and CFSE labeled. One million CFSE labeled DC were injected intradermally into the flank. After 2 days, the inguinal lymph node was dissected and processed to obtain a single cell suspension. The suspension was analyzed by flow cytometry and CFSE positive DC were counted (FIGS. 11A, 11B, and 11C). Only background levels of migration were detected in the no treatment control (FIGS. 11D and 11E).
Figures 11D, 11E, 11F, 11G, 11H, 11I:
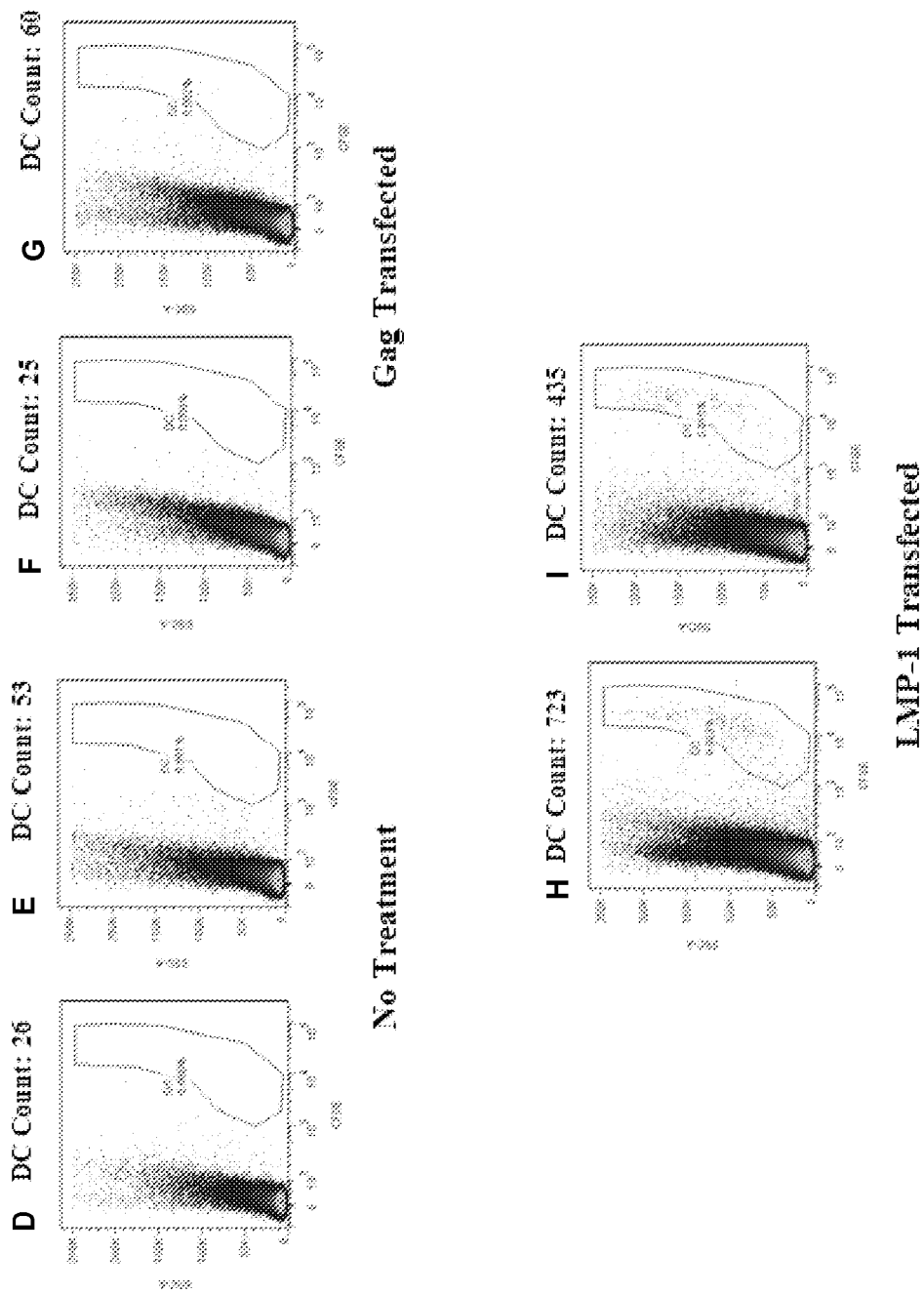

Referring to FIGS. 11A-11I, LMP1 induces DC migration in vivo in Balb/c mice. Bone-marrow derived DC were generated by a five day culture with mGM-CSF and mIL-4. Cells were harvested and either put into culture with the Mimic cytokine cocktail (FIG. 11C) or electroporated with 10 μg Gag mRNA (FIGS. 11F and 11G) or 10 μg LMP1 mRNA (FIGS. 11H and 11I). After 36 hours of maturation, cells were washed and CFSE labeled. One million CFSE labeled DC were injected intradermally into the flank. After 2 days, the inguinal lymph node was dissected and processed to obtain a single cell suspension. The suspension was analyzed by flow cytometry and the CFSE positive DC were counted. (FIGS. 11A, 11B, and 11C). The negative PBS control reported minimal background levels. (FIG. 11A). Unlike in human DC, immature BMDC do possess migratory abilities. When DC were matured with Mimic+$PGE_2$, these levels were 2.5 times greater, suggesting that maturation still increases migration rates. (FIG. 11C). This increase in migration is consistent with observations in human DC.

LMP1 increases migration rates in mouse bone marrow-derived dendritic cells in the absence of $PGE_2$. In order to determine if LMP1 increases mouse BMDC migration rates as it does in humans, immature BMDC were transfected with mRNA encoding LMP1 or Gag as a RNA control treatment. These DC were then matured in Mimic cocktail without $PGE_2$ and injected into the mice. After 48 hours, migrated DC were counted in the inguinal lymph nodes.

Only background levels of migration were detected in the no treatment control. (FIGS. 11D and 11E). These levels were identical to the Gag transfected DC control suggesting that RNA transfection alone does not induce DC migration. (FIGS. 11F and 11G). LMP1 transfection did increase migration rates. (FIGS. 11H and 11I). A distinct population of cells is visible when run on a flow cytometer. Although these migration rates are significantly less than what is seen in vitro, these results still suggest that LMP1 does indeed increase the functional ability of DC to migrate to a draining lymph node.

Example 11

Figures 12A, 12B:
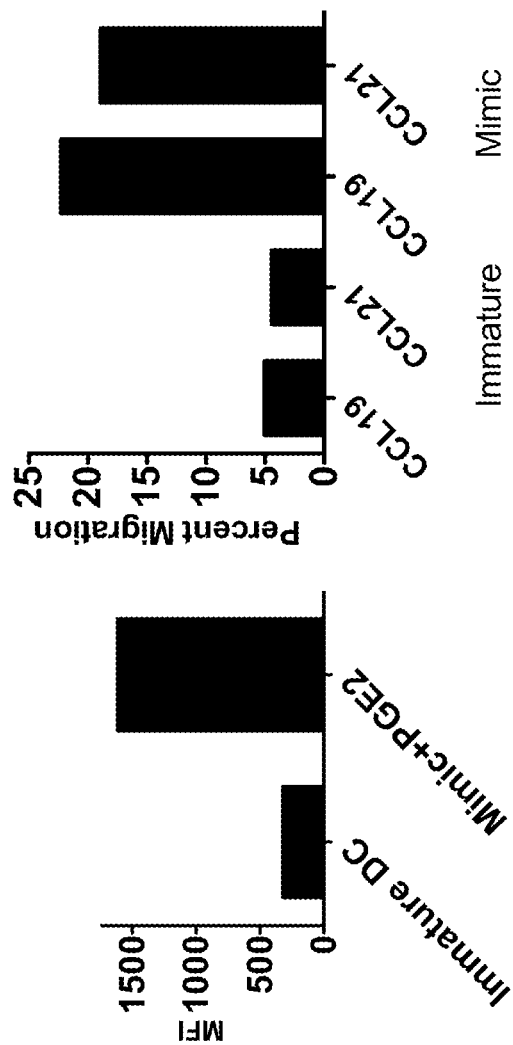
FIGS. 12A and 12B show that Mimic maturation induces CCR7 expression and DC migration. On day 5 non-adherent immature DC were removed from culture and matured. CCR7 expression was determined by immuno-staining and flow cytometric analysis 48 hours after maturation.

Referring to FIGS. 12A and 12B, Mimic maturation induces CCR7 expression and DC migration. Monocyte derived dendritic cells were generated as follows: Isolated monocytes were cultured for 5 days in human DC media supplemented with GM-CSF, 1000 U/mL (BERLEX Inc.), and IL-4, 500 U/mL (R&D Systems). To harvest immature DC, the flasks were placed at 4° C. for 30 minutes. Non-adherent and semi-adherent dendritic cells were collected by washing the flasks three times with cold PBS. The remaining adherent cells were discarded.

On day 5 non-adherent immature DC were removed from culture and matured. CCR7 expression was determined by immuno-staining and flow cytometric analysis 48 hours after maturation. (FIG. 12A). DC's migratory ability were tested using an 8 μm pore Transwell®. (FIG. 12B). 150,000 cells were allowed 90 minutes to migrate in response to CCL19 or CCL21.

Dendritic cell maturation with $PGE_2$ induced CCR7 expression and migration in human MDDC. $PGE_2$ has been known to cause various side effects in MDDC. Therefore, it was studied whether immature DC possess the same ability to migrate as Mimic matured DC. Surface expression of CCR7 was studied to see if maturation upregulated a key chemokine receptor necessary for migration to the draining lymph node. (FIG. 12A). Immature DC were matured for 36 hours in the presence of Mimic and $PGE_2$, then stained from CCR7 expression and analyzed by flow cytometry. Mimic maturation with $PGE_2$ significantly increases surface expression of CCR7, suggesting better rates of migration.

To test migration, the same cells were give 90 minutes to migrate to either CCL19 or CCL21 (chemokines for CCR7) in the Transwell® migration assay. Immature DC showed low levels of migration, around 5%, to both CCL19 and CCL21. (FIG. 12B). As expected, Mimic matured DC migrated to CCL19 and CCL21 at a 4 fold higher rate. This suggested that maturation is key for DC migration.

Example 12

Figure 13A:
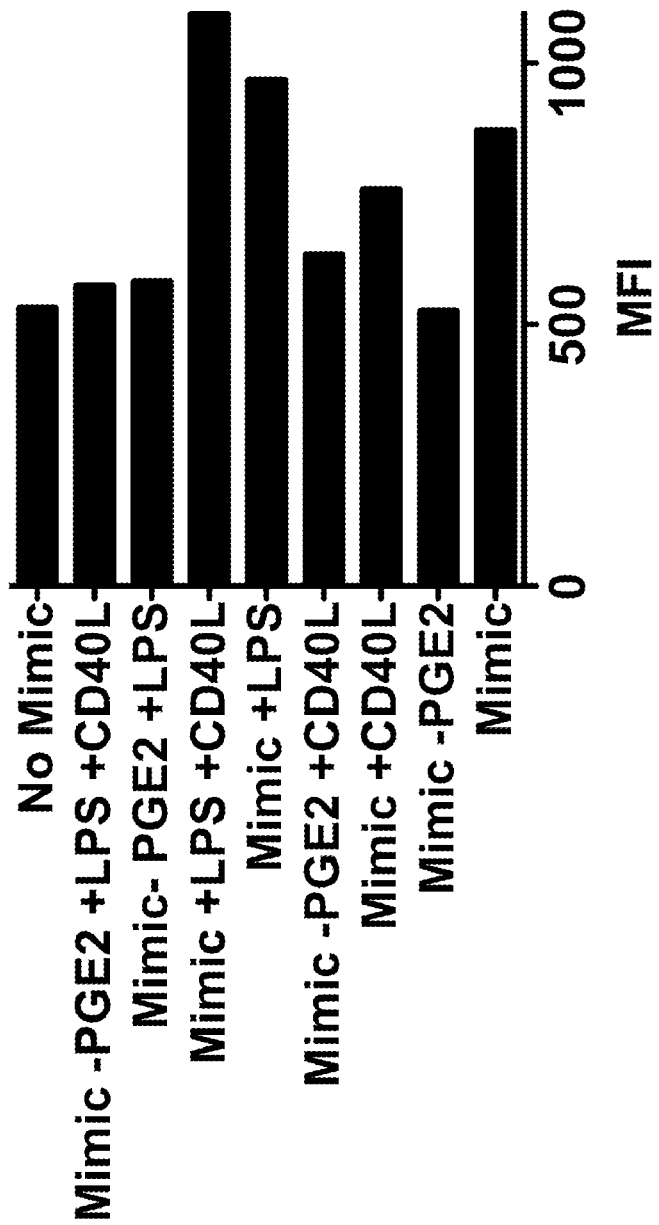
FIGS. 13A and 13B show that $PGE_2$ causes MDDC migration and correlates with CCR7 expression. Five days immature DC were stimulated with either Mega-CD40L™ or LPS in the presence or absence of $PGE_2$. CCR7 expression levels were evaluated by immuno-staining and flow cytometric analysis 48 hours after maturation.
Figure 13B:
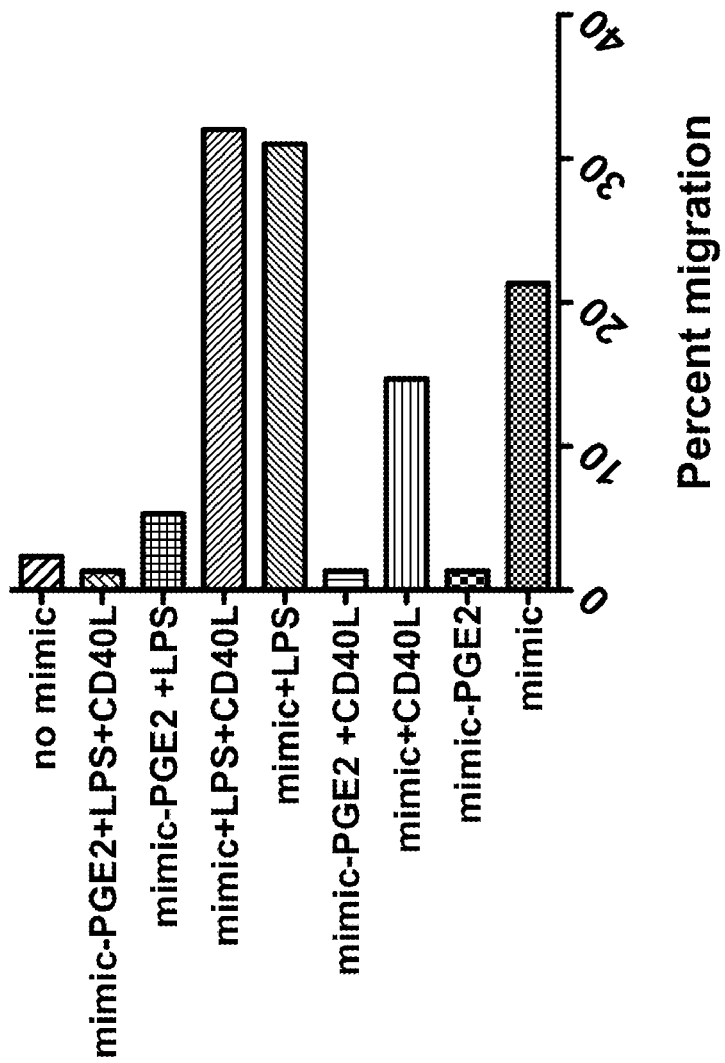

Referring to FIGS. 13A and 13B, $PGE_2$ is necessary for MDDC migration and correlates with CCR7 expression. Five days immature DC were stimulated with either Mega-CD40L™ or LPS in the presence or absence of $PGE_2$. CCR7 expression levels were evaluated by immuno-staining and flow cytometric analysis 48 hours after maturation. (FIG. 13A). The migratory ability of DCs was tested using an 8 μm pore Transwell®. (FIG. 13B). 150,000 cells were allowed 90 minutes to migrate in response to CCL19.

$PGE_2$ induces in vitro DC migration. Since maturation appeared to be an important part of DC migration, it was studied whether there was a suitable replacement for $PGE_2$ that would allow the same functional benefits, while eliminating some of the negative side effects. Five day immature monocyte-derived dendritic cells were matured with a combination of immunostimulants including Mimic, $PGE_2$, Mega-CD40L™, and LPS. After 48 hours, DC were harvested and stained for CCR7 expression and analyzed by flow cytometry.

Forms of maturation that did not include $PGE_2$ failed to increase levels of surface CCR7 expression (FIG. 13A). These protocols expression levels were similar to the basal level of expression seen on immature DC. However, the addition of $PGE_2$ to the maturation cocktail significantly increased CCR7 levels. This expression level seemed to be additive, in that the more immunostimulants added, the higher the level of CCR7 expression. (FIG. 13A).

$PGE_2$ induces dendritic cell migration in vitro. In vitro migration was tested to see if levels of CCR7 expression correlate to the functional ability of DCs to migrate to chemokines Migration was tested using a Transwell® migration assay to CCL19.

In the absence of any maturation cocktail, DC migration is negligible (below 5%). Similar to observations in CCR7 expression, any maturation protocol that did not contain $PGE_2$ yielded a DC that was incapable of migrating to CCL19. (FIG. 13B). However, after the addition of $PGE_2$ to the cocktail, DC maturation was significantly increased (20-35%). Interestingly, the addition of Mega-CD40L™ to Mimic+$PGE_2$ actually decreases migration when compared to Mimic+$PGE_2$ alone, similar to the decrease that was seen in CCR7 expression. The addition of LPS along with Mimic and $PGE_2$ yielded the best migration (31%). The addition of Mega-CD40L to this mixture had very minimal benefits only increasing the migration by 1%.

Example 13

Figure 14A:
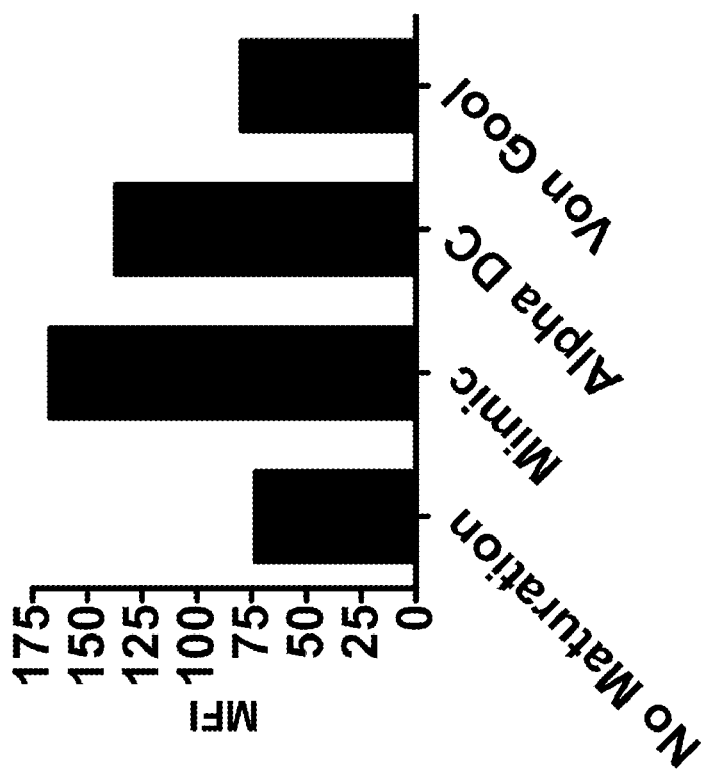
FIGS. 14A and 14B show that Mimic maturation matures a migratory DC. Five day non-adherent immature DC were removed from culture and matured using three classic protocols found in the literature: Mimic matured, Alpha DC, and Von Gool DC. CCR7 expression was assessed by flow cytometry.
Figure 14B:
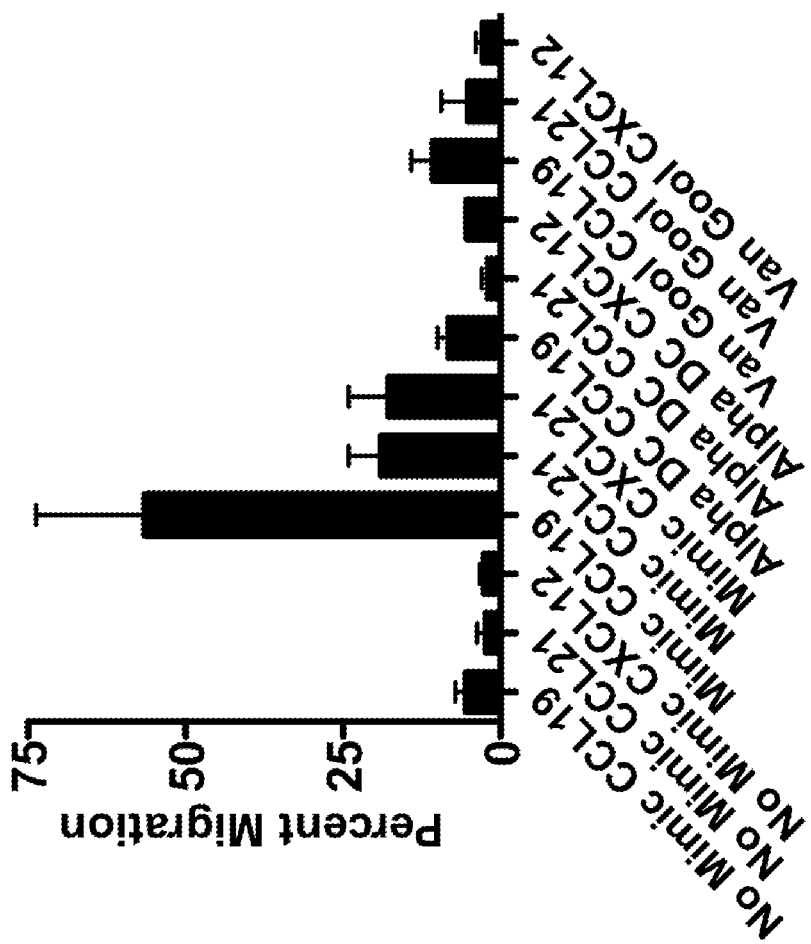

Referring to FIGS. 14A and 14B, the Mimic maturation protocol matured a migratory DC. Five day non-adherent immature DC were removed from culture and matured using three classic protocols found in the literature: Mimic matured, Alpha DC, and Von Gool DC. The Mimic matured, Alpha DC, and Von Gool DC maturation protocols are as follows: (1) Mimic matured cytokine mix (5 ng/mL of TNF-α [R&D)], 5 ng/mL of IL-1β [R&D], 750 ng/mL of IL-6 [R&D], and 1 μg/mL of $PGE_2$ [Sigma]), (2) Alpha DC cytokine mix (3000 U/ml TNF-α, 1000 U/ml IFN-γ, and 20 μg/ml polyinosinic: polycytidylic acid (Poly I:C)), or (3) Von Gool DC cytokine mix (2000 U/ml IL-1β and 1000 U/ml TNF-α). The cells were cultured for 36 hours at 37° C. in 5% $CO_2$ and then used for migration assays.

CCR7 expression was assessed by flow cytometry. (FIG. 14A). The migratory ability of the DCs was tested using an 8 μm pore Transwell®. (FIG. 14B). 150,000 cells were allowed 90 minutes to migrate in response to CCL19, CCL21, or CXCL12.

Mimic-matured dendritic cells express the highest amounts of CCR7 compared to common maturation protocols. It appears that $PGE_2$ is necessary to induce CCR7 expression and DC migration. Common maturation protocols that do not include $PGE_2$ were tested to see if migration could be induced without the use of $PGE_2$. Three common maturation protocols were used to mature DC: Mimic matured, Alpha DC, and Von Gool DC. After maturation, cells were stained with CCR7 and analyzed by flow cytometry (FIG. 14A). The Von Gool protocol failed to induce any CCR7 expression over normal levels on immature DC. The Alpha DC protocol induced modest CCR7 expression but levels were much lower than the classic Mimic matured DC. (FIG. 14A).

Mimic maturation induces the best migration rates in MDDC. All three common protocols were tested against CCL19, CCL21, and CXCL12 to determine if certain protocols gave preferential migration to certain chemokines (FIG. 14B). Mimic maturation yielded the highest migration rates to CCL19 (56%). Mimic DC also migrated to both CCL21 and CXCL12 but at a much lower levels than CCL19 (~22%). Although Alpha DC showed modest CCR7 expression, migration rates did not correlate. Levels were comparable to that of immature DC. DC matured using the Von Gool protocol did not migrate to any chemokine (FIG. 14B).

Example 14

Figure 15A:
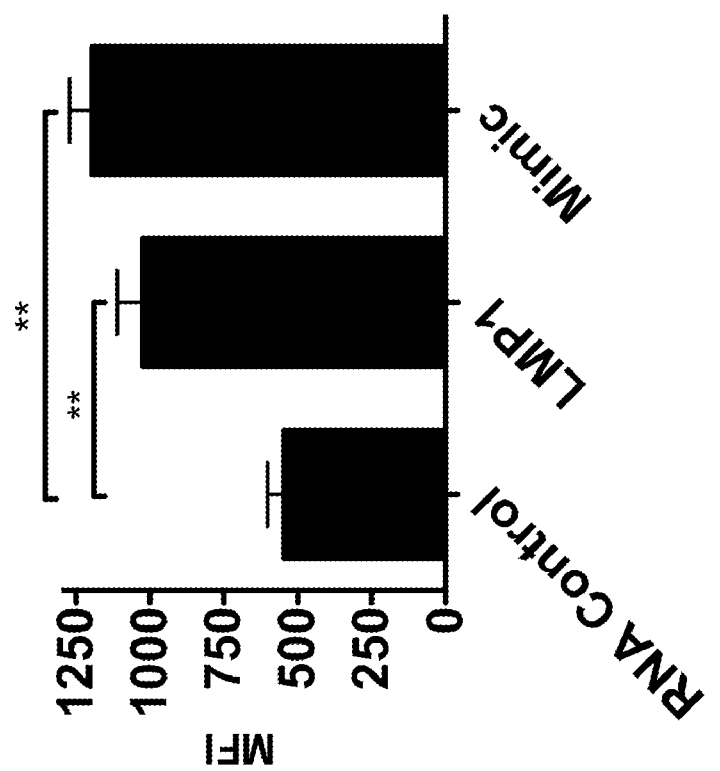
FIGS. 15A and 15B show that Transwell® migration of human monocyte-derived mRNA transfected dendritic cells were matured with various protocols. Day 5 non-adherent DC were electroporated with 10 ug mRNA encoding either LMP1, LMP1-CD40, or GFP control RNA. CCR7 levels were analyzed by immuno-staining and flow cytometric analysis. RNA control and LMP1 transfected cells, which received no further maturation, were compared to non-transfected Mimic+$PGE_2$ matured DC.
Figure 15B:
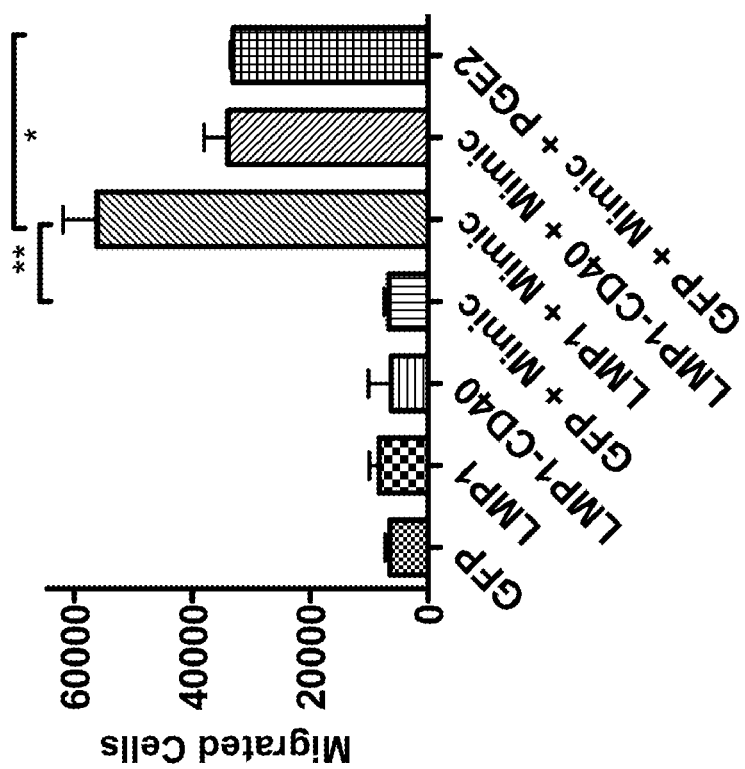

Referring to FIGS. 15A and 15B, Transwell® migration of human monocyte-derived mRNA transfected dendritic cells were matured with various protocols. Day 5 non-adherent DC were electroporated with 10 μg mRNA encoding either LMP1, LMP1-CD40, or GFP control RNA. CCR7 levels were analyzed by immuno-staining and flow cytometric analysis. RNA control and LMP1 transfected cells, which received no further maturation, were compared to non-transfected Mimic+$PGE_2$ matured DC. (FIG. 15A). Migratory ability was determined using the Transwell® migration assay in response to CCL19. (FIG. 15B).

LMP1 induced CCR7 expression. LMP1 also induced migration levels greater than that of Mimic matured DC. Immature human dendritic cells obtained from buffy coats were transfected with mRNA encoding molecular adjuvants LMP1 or LMP1-CD40. After 48 hours, CCR7 levels were measured by flow cytometry. (FIG. 15A). LMP1-transfected DC significantly upregulated CCR7 to levels similar to those of DC matured with Mimic+$PGE_2$. This finding suggested that LMP1 may give DC the functional ability to migrate without the use of $PGE_2$. To test this, DC were transfected and matured with or without Mimic. (FIG. 15B). Interestingly, LMP1 and LMP1-CD40 transfected DC could not migrate to CCL19 even though they express high levels of CCR7. When transfected DC were matured with Mimic without $PGE_2$, migration was achieved. LMP1-CD40 transfected DC+Mimic migrated as well as Mimic+$PGE_2$ DC. When LMP1 transfected DC were matured with Mimic without PGE2, they achieved migration rate almost twice that of Mimic+$PGE_2$. These data suggest that LMP1 may be a superior replacement for $PGE_2$ when maturing monocyte-derived dendritic cells.

Other Embodiments

Any improvement may be made in part or all of the compositions, kits, and method steps. All references, including publications, patent applications, and patents, cited herein are hereby incorporated by reference. The use of any and all examples, or exemplary language (e.g., "such as") provided herein, is intended to illuminate the invention and does not pose a limitation on the scope of the invention unless otherwise claimed. Any statement herein as to the nature or benefits of the invention or of the preferred embodiments is not intended to be limiting, and the appended claims should not be deemed to be limited by such statements. More generally, no language in the specification should be construed as indicating any non-claimed element as being essential to the practice of the invention. This invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contraindicated by context.

REFERENCES

Advances in Immunology, volume 93, ed. Frederick W. Alt, Academic Press, Burlington, Mass., (2007)

BD Cytometric Bead Array (CBA) Human Inflammatory Cytokines Kit Instruction Manual, Becton, Dickinson, and Company, (2010).

Current Protocols in Immunology, ed. Coligan et al., Greene Publishing and Wiley-Interscience, New York, (1992) (with periodic updates).

Current Protocols in Molecular Biology, ed. Ausubel et al., Greene Publishing and Wiley-Interscience, New York, (1992) (with periodic updates).

Encyclopedia of Pharmaceutical Technology, eds. J. Swarbrick and J. C. Boylan, Marcel Dekker, New York (1988-1999)).

Gilboa, E., DC-based cancer vaccines. J Clin Invest, 117(5): 1195-203 (2007)

Harlow and Lane ANTIBODIES: A Laboratory Manual, Cold Spring Harbor Laboratory Press, Cold Spring Harbor, N.Y., (1988).

Kornbluth, R. S. and Stone, G. W., Immunostimulatory combinations: designing the next generation of vaccine adjuvants. J Leukoc Biol, 80(5): 1084-102 (2006).

Lu, W., et al., Therapeutic dendritic-cell vaccine for chronic HIV-1 infection. Nat Med,. 10(12): 1359-65 (2004).

Making and Using Antibodies: A Practical Handbook, eds. Gary C. Howard and Matthew R. Kaser, CRC Press, Boca Raton, Fla., (2006)

Medical Immunology, 6th ed., edited by Gabriel Virella, Informa Healthcare Press, London, England, (2007)

Molecular Cloning: A Laboratory Manual, 3rd ed., vol. 1-3, ed. Sambrook et al., Cold Spring Harbor Laboratory Press, Cold Spring Harbor, N.Y., (2001).

Remington: The Science and Practice of Pharmacy (20th ed.), ed. A. R. Gennaro, Lippincott Williams & Wilkins, (2000).

Stone, G. W. et al., Multimeric soluble CD40 ligand and GITR ligand as adjuvants for human immunodeficiency virus DNA vaccines. J Virol, 80(4): 1762-72 (2006).

What is claimed is:

1. A composition comprising dendritic cells transfected with a nucleic acid sequence encoding a full-length latent membrane protein (LMP1) protein, wherein the dendritic cells are capable of migrating towards lymph node chemokines, secreting IL-12 and activating T cells.

2. The composition of claim 1, wherein the nucleic acid is RNA.

3. The composition of claim 1, further comprising a media formulation comprising at least one cytokine selected from the group consisting of: IL-1β, TNFα, and IL-6.

4. The composition of claim 3, wherein the at least one cytokine consists of: IL-1β, TNFα, and IL-6.

5. The composition of claim 1, wherein the dendritic cells are human dendritic cells.

6. A composition for inducing dendritic cell migration comprising:
    (i) a full-length LMP1-CD40 chimeric protein or a nucleic acid sequence encoding a full-length LMP1-CD40 chimeric protein,
    (ii) IL-1β, TNFα and IL-6,
    wherein dendritic cells that are contacted with said composition are capable of migrating towards lymph node chemokines, secreting IL-12 and activating T cells.

7. The composition of claim 6, wherein the composition is a vaccine adjuvant for treating a disease or condition in a subject, and further comprises a pharmaceutically acceptable excipient.

8. A composition comprising dendritic cells transfected with a nucleic acid sequence encoding a full-length LMP1-CD40 chimeric protein, wherein the dendritic cells are capable of migrating towards lymph node chemokines, secreting IL-12 and activating T cells.

* * * * *